US010317346B2

(12) United States Patent
Fujiwara

(10) Patent No.: US 10,317,346 B2
(45) Date of Patent: Jun. 11, 2019

(54) METHOD AND DEVICE FOR INSPECTING SPATIAL LIGHT MODULATOR, AND EXPOSURE METHOD AND DEVICE

(75) Inventor: Tomoharu Fujiwara, Gyoda (JP)

(73) Assignee: NIKON CORPORATION, Tokyo (JP)

( * ) Notice: Subject to any disclaimer, the term of this patent is extended or adjusted under 35 U.S.C. 154(b) by 271 days.

(21) Appl. No.: 14/241,951

(22) PCT Filed: Aug. 30, 2012

(86) PCT No.: PCT/JP2012/072025
§ 371 (c)(1),
(2), (4) Date: May 2, 2014

(87) PCT Pub. No.: WO2013/031901
PCT Pub. Date: Mar. 7, 2013

(65) Prior Publication Data
US 2014/0320835 A1    Oct. 30, 2014

(30) Foreign Application Priority Data
Sep. 2, 2011 (JP) .............................. P2011-191319

(51) Int. Cl.
*G03B 27/54* (2006.01)
*G01N 21/95* (2006.01)
(Continued)

(52) U.S. Cl.
CPC ............. *G01N 21/95* (2013.01); *G01N 21/55* (2013.01); *G02B 26/06* (2013.01);
(Continued)

(58) Field of Classification Search
CPC ............. G03F 7/70058; G03F 7/70291; G03F 7/70425; G03F 7/7065; G02B 26/06
(Continued)

(56) References Cited

U.S. PATENT DOCUMENTS 6,215,578 B1 * 4/2001 Lin .................... G03F 7/70091
355/53
6,847,752 B2 * 1/2005 Nemirovsky ...... G02B 26/0841
385/18
(Continued)

FOREIGN PATENT DOCUMENTS

JP    2001-013427 A    1/2001
JP    2005-510862 A    4/2005
(Continued)

OTHER PUBLICATIONS

López, D., et al., "Two-dimensional MEMS array for maskless lithography and wavefront modulation", Proceeding of SPIE (US), vol. 6589, 2007, pp. 65890S-1~65890S-8.
(Continued)

*Primary Examiner* — Peter B Kim
(74) *Attorney, Agent, or Firm* — Shapiro, Gabor and Rosenberger, PLLC

(57) ABSTRACT

A method for inspecting a spatial light modulator includes: performing such control that in an inspection target area in an array of mirror elements, the mirror elements in a first state in which incident light is given a phase change amount of 0 and the mirror elements in a second state in which incident light is given a phase change amount of 180° (π) become arrayed in a checkered pattern; guiding light having passed the inspection target area to a projection optical system with a resolution limit coarser than a width of an image of one mirror element, to form a spatial image; and inspecting a characteristic of the spatial light modulator from the spatial image. This method allows us to readily perform the inspection of the characteristic of the spatial light modulator having the array of optical elements.

10 Claims, 15 Drawing Sheets

(51) Int. Cl.
*G02B 26/06* (2006.01)
*G03F 7/20* (2006.01)
*G06T 7/00* (2017.01)
*G01N 21/55* (2014.01)

(52) U.S. Cl.
CPC ........ *G03F 7/70058* (2013.01); *G03F 7/7065* (2013.01); *G03F 7/70291* (2013.01); *G03F 7/70425* (2013.01); *G06T 7/0004* (2013.01); *G01N 2021/9511* (2013.01); *G06T 2207/10061* (2013.01); *G06T 2207/30148* (2013.01)

(58) Field of Classification Search
USPC .......................................................... 355/67
See application file for complete search history.

(56) References Cited

U.S. PATENT DOCUMENTS

| | | | |
|---|---|---|---|
| 2002/0024714 A1* | 2/2002 | Sandstrom | G02B 26/0833 359/290 |
| 2002/0114558 A1 | 8/2002 | Nemirovsky | |
| 2003/0099026 A1 | 5/2003 | Sandstrom | |
| 2004/0047023 A1 | 3/2004 | Sandstrom | |
| 2004/0207386 A1 | 10/2004 | Durr | |
| 2005/0007603 A1* | 1/2005 | Arieli | G01J 9/02 356/601 |
| 2007/0242247 A1 | 10/2007 | Shiraishi | |
| 2008/0239421 A1 | 10/2008 | Yoshikawa et al. | |
| 2008/0304030 A1 | 12/2008 | Lous | |
| 2008/0309898 A1 | 12/2008 | Baselmans | |
| 2008/0309899 A1 | 12/2008 | Baselmans et al. | |
| 2009/0303571 A1* | 12/2009 | Sandstrom | G02B 5/1809 359/291 |

FOREIGN PATENT DOCUMENTS

| | | | |
|---|---|---|---|
| JP | 2005-326465 A | 11/2005 | |
| JP | 2006-516724 A | 7/2006 | |
| JP | 2008-541164 A | 11/2008 | |
| JP | 2010-002776 A | 1/2010 | |
| JP | 2010-530615 A | 9/2010 | |
| JP | WO 2012081292 A1 * | 6/2012 | ............ G02B 26/06 |
| KR | 10-0474121 B1 | 5/2005 | |
| KR | 2005-0086953 A | 8/2005 | |
| KR | 2008-0051183 A | 6/2008 | |
| WO | WO 99/45437 | 9/1999 | |
| WO | WO 2007/049383 A1 | 5/2007 | |
| WO | WO 2012000528 A1 * | 1/2012 | ............ G02B 26/06 |

OTHER PUBLICATIONS

International Search Report from International Patent Application No. PCT/JP2012/072025, dated Oct. 9, 2012.
Office Action dated May 15, 2018, in Korean Patent Application No. 10-2014-7008802.
Office Action dated Mar. 26, 2019, in Korean Patent Application No. 10-2014-7008802.

* cited by examiner

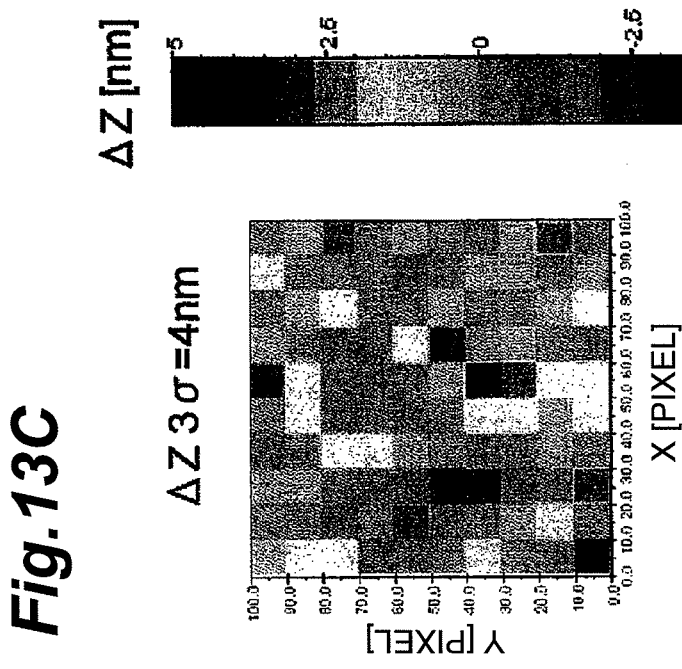
Fig. 13A  ΔZ 3σ=1nm
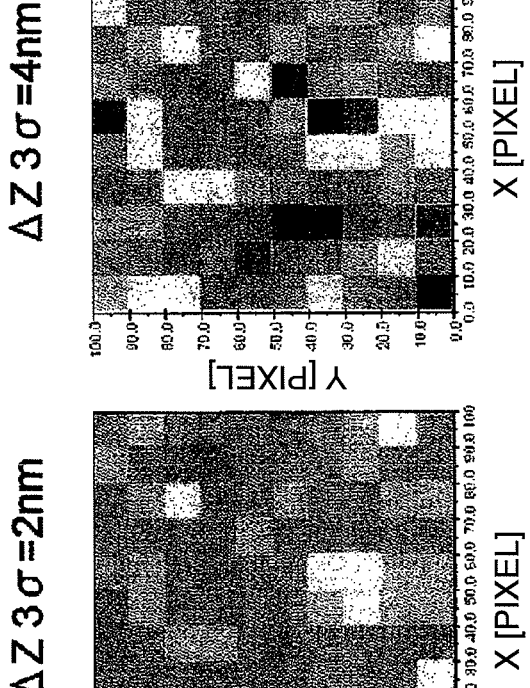
Fig. 13B  ΔZ 3σ=2nm
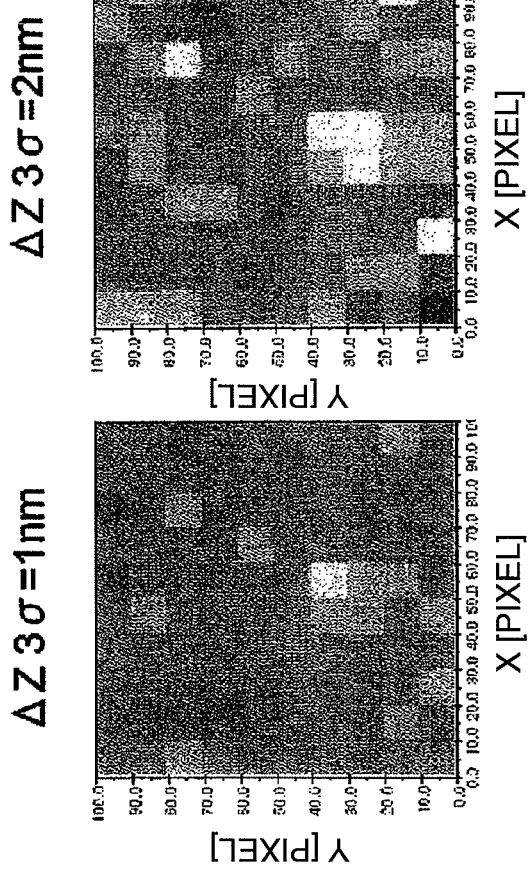
Fig. 13C  ΔZ 3σ=4nm

METHOD AND DEVICE FOR INSPECTING SPATIAL LIGHT MODULATOR, AND EXPOSURE METHOD AND DEVICE

TECHNICAL FIELD

The present invention relates to an inspection technology for inspecting a spatial light modulator having a plurality of optical elements, an exposure technology for exposing an object with use of this inspection technology, and a device manufacturing technology making use of this exposure technology.

BACKGROUND ART

The exposure apparatus of a one-shot exposure type such as steppers or the exposure apparatus of a scanning exposure type such as scanning steppers are used for forming a predetermined pattern in each shot area on a substrate such as a wafer or a glass plate through a projection optical system, for example, in a lithography process for manufacturing devices (electronic devices or microdevices) such as semiconductor devices or liquid crystal display devices.

There is the recently-proposed exposure apparatus of a so-called maskless method to generate a variable pattern on the object plane of the projection optical system, using spatial light modulators (SLM) having an array of many microscopic mirrors an inclination angle of each of which is variable, instead of masks, for efficiently manufacturing each of devices while suppressing an increase of manufacturing cost due to preparation of masks for respective types of devices and masks for respective layers on the substrate (e.g., cf. Patent Literature 1). There are also the proposed spatial light modulators of a type having an array of many microscopic mirrors a height of a reflective surface of each of which is controllable, in order to control a phase distribution of incident light (e.g., cf. Non Patent Literature 1).

CITATION LIST

Patent Literature

Patent Literature 1: U.S. Pat. Published Application No. 2008/0309898

Non Patent Literature

Non Patent Literature 1: D. Lopez et al., "Two-dimensional MEMS array for maskless lithography and wavefront modulation," Proc. of SPIE (U.S.A.) Vol. 6589, 65890S (2007)

SUMMARY OF INVENTION

Technical Problem

If in use of the spatial light modulator having the array of many microscopic mirrors, there is a microscopic mirror (defective element) failing to undergo accurate control of height in the array or there occurs such a phenomenon that curvature of a reflective surface of the spatial light modulator is over a tolerance, an intensity distribution of a spatial image finally formed on the surface of the substrate could deviate from a target distribution.

For performing an inspection of a characteristic of the defective element or the like in the spatial light modulator, it is preferable to allow easy execution of the inspection in an on-body condition, for example, without dismounting the spatial light modulator from an exposure device.

In light of the above-described circumstances, it is an object of the present invention to implement easy execution of an inspection of a characteristic of a spatial light modulator having an array of optical elements.

Solution to Problem

A first aspect of the present invention provides a method for inspecting a spatial light modulator having an array of optical elements to be illuminated with light. This inspection method is one comprising: performing such control that in at least a partial inspection target area in the array of optical elements, the optical elements in a first state which allow incident light to pass with a phase change of a first phase and the optical elements in a second state which allow incident light to pass with a phase change of a second phase 180° different from the first phase become arrayed in a checkered pattern; guiding light having passed the inspection target area to a projection optical system with a resolution limit coarser than a width of an image of one optical element, to form a spatial image; and inspecting a characteristic of the spatial light modulator from the spatial image formed by the projection optical system.

A second aspect provides an apparatus for inspecting a spatial light modulator having an array of optical elements to be illuminated with light. This inspection apparatus is one comprising: an illumination apparatus which illuminates at least a partial inspection target area in the array of optical elements; a control apparatus which performs such control that in the inspection target area, the optical elements in a first state which allow incident light to pass with a phase change of a first phase and the optical elements in a second state which allow incident light to pass with a phase change of a second phase 180° different from the first phase become arrayed in a checkered pattern; a projection optical system which forms a spatial image from light having passed the inspection target area and which has a resolution limit coarser than a width of an image of one optical element; and an arithmetic apparatus which performs an inspection of the spatial light modulator, on the spatial image formed by the projection optical system.

A third aspect provides an exposure method for exposing a substrate with exposure light via a spatial light modulator having an array of optical elements and via a projection optical system, the exposure method comprising a step of performing an inspection of the spatial light modulator by the inspection method for the spatial light modulator of the present invention.

A fourth aspect provides an exposure apparatus for exposing a substrate with exposure light from an illumination system via a projection system. This exposure apparatus is one comprising: a spatial light modulator which is arranged on the object plane side of the projection system and which has an array of optical elements each of which can be controlled so as to guide the exposure light to the projection system; and the inspection apparatus for the spatial light modulator of the present invention.

A fifth aspect provides a device manufacturing method comprising: forming a pattern of a photosensitive layer on a substrate, using the exposure method or the exposure apparatus of the present invention; and processing the substrate with the pattern formed thereon.

Advantageous Effect of Invention

According to the present invention, the optical elements in the first state and the optical elements in the second state are arrayed in the checkered pattern in the inspection target area in the array of optical elements of the spatial light modulator and the light from the inspection target area is guided to the projection optical system with the resolution limit coarser than the width of the image of one optical element to form the spatial image, whereby if there is a difference between a characteristic of the optical element array and a target characteristic an intensity distribution of the spatial image will change from an almost-constant low-level distribution. Therefore, the inspection of the characteristic of the spatial light modulator can be readily preformed with the use of the spatial image.

BRIEF DESCRIPTION OF DRAWINGS

FIG. 13A, FIG. 13B, and FIG. 13C are drawings showing an example of height distributions in cases where mirror elements of the spatial light modulator have height variations of 1 nm, 2 nm, and 4 nm, respectively.

DESCRIPTION OF EMBODIMENTS

First Embodiment

The first embodiment will be described below with reference to FIGS. 1, 2A to 6D, and 7.

Figure 1:
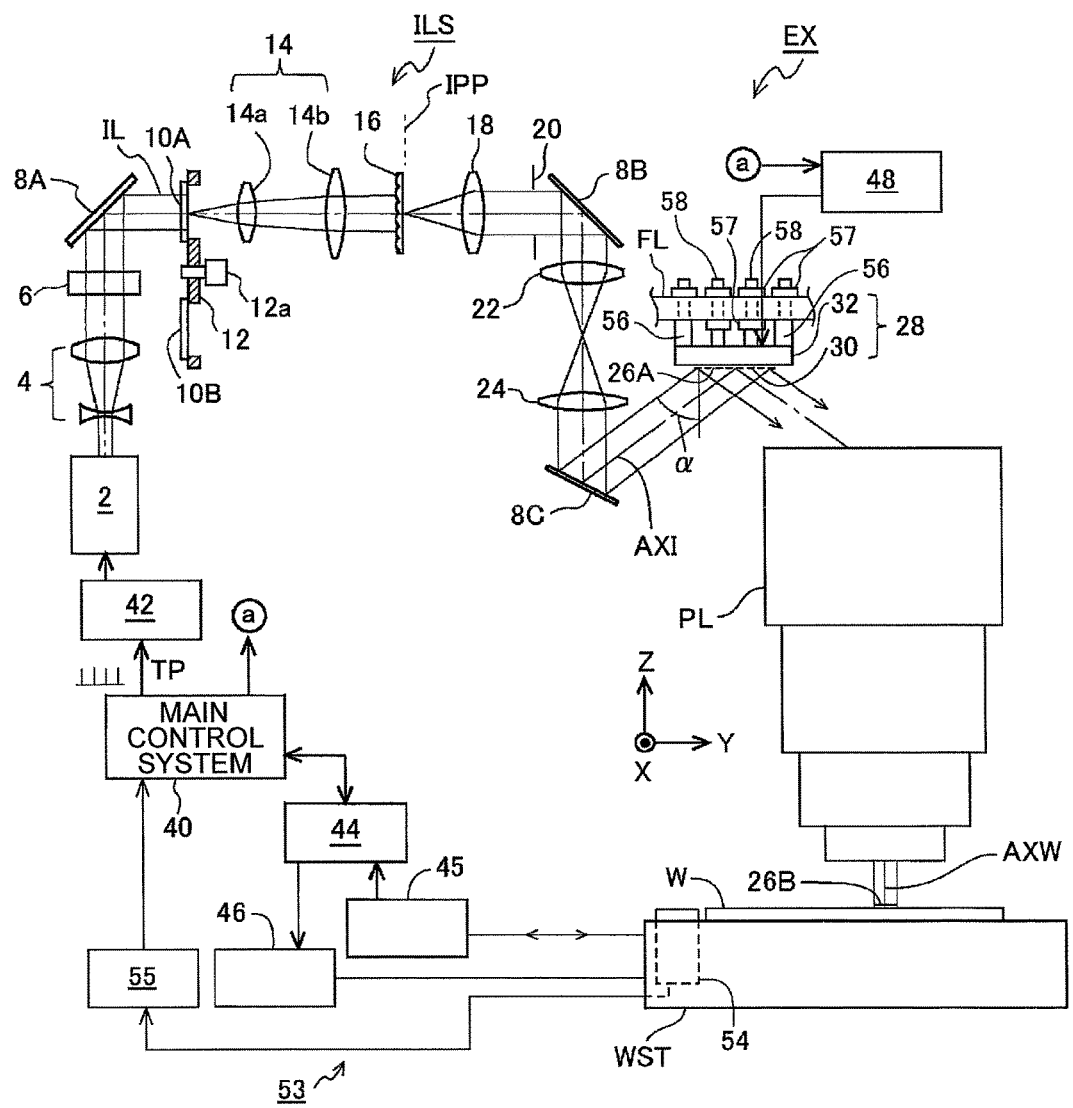
FIG. 1 is a drawing showing a schematic configuration of an exposure apparatus as an example of embodiment.

FIG. 1 shows a schematic configuration of an exposure apparatus EX of the maskless method according to the present embodiment. In FIG. 1, the exposure apparatus EX has a light source 2 for exposure which emits pulses of light, an illumination optical system ILS which illuminates an illumination target surface with illumination light (exposure light) IL for exposure from the light source 2, a spatial light modulator 28 with a large number of mirror elements 30 which are respective height-variable microscopic mirrors arranged in a two-dimensional array pattern approximately on the illumination target surface or on a surface near it, a modulation control unit 48 which drives the spatial light modulator 28, and an inspection apparatus 53 for the spatial light modulator 28. Furthermore, the exposure apparatus EX has a projection optical system PL which receives the illumination light IL reflected by a reflective, variable, uneven pattern (mask pattern with a variable phase distribution) generated by the large number of mirror elements 30 and which projects a spatial image (device pattern) formed corresponding to the uneven pattern (phase distribution), onto a surface of a wafer W (substrate), a wafer stage WST which performs positioning and movement of the wafer W, a main control system 40 consisting of a computer which generally controls the operation of the overall apparatus, various control systems, and so on.

The description hereinafter will be based on such a coordinate system that in FIG. 1, the Z-axis is set along a direction perpendicular to a bottom surface of the wafer stage WST (a plane parallel to an unrepresented guide surface), the Y-axis is set along a direction parallel to the plane of FIG. 1 in a plane normal to the Z-axis, and the X-axis is set along a direction normal to the plane of FIG. 1. Angles around the X-axis, Y-axis, and Z-axis will also be called angles in θx direction, θy direction, and θz direction, respectively. In the present embodiment, the wafer W is scanned in the Y-direction (scanning direction) during exposure.

The light source 2 used herein is an ArF excimer laser light source which emits pulses of substantially linearly polarized laser light with the wavelength of 193 nm and the pulse width of about 50 ns, at the frequency of approximately 4-6 kHz. The light source 2 also applicable herein can be, for example, a KrF excimer laser light source with the wavelength of 248 nm, a light emitting diode which emits pulsed light, or a solid-state pulsed laser light source which generates a harmonic of laser light output from a YAG laser or a solid-state laser (semiconductor laser or the like). The solid-state pulsed laser light source can emit pulses of laser light, e.g., with the wavelength of 193 nm (or any one of various wavelengths except for it) and with the pulse width of about 1 ns, at the frequency of approximately 1-2 MHz.

In the present embodiment, a power supply 42 is connected to the light source 2. The main control system 40 supplies to the power supply 42, emission trigger pulses TP indicative of timing and light quantity (pulse energy) of pulsed emission. In synchronism with the emission trigger pulses TP, the power supply 42 makes the light source 2 emit pulses at the indicated timing and light quantity.

The illumination light IL consisting of a substantially parallel beam of pulsed laser light with a rectangular sectional shape emitted from the light source 2 travels via a beam expander 4 consisting of a pair of lenses, via a polarization control optical system 6 to control a state of polarization of the illumination light IL, and via a mirror 8A, to enter a diffractive optical element (diffractive optical element 10A in FIG. 1) selected from a plurality of diffractive optical elements 10A, 10B, and so on, in parallel with the Y-axis. The polarization control optical system 6 is, for example, an optical system that can replaceably set one of a half wave plate to rotate the direction of polarization of the illumination light IL, a quarter wave plate to convert the illumination light IL into circularly polarized light, and a birefringent prism of a wedge shape to convert the illumination light IL into randomly polarized light (unpolarized light).

The diffractive optical elements 10A, 10B, etc. are fixed at approximately equal angle intervals to a peripheral part of a rotary plate 12. The main control system 40 controls the angle of the rotary plate 12 through a drive unit 12a, to set a diffractive optical element selected according to an illumination condition, on the optical path of the illumination light IL. The illumination light IL diffracted by the selected diffractive optical element is guided to an entrance plane of a microlens array 16 by a relay optical system 14 consisting of lenses 14a, 14b. The illumination light IL incident into the microlens array 16 is two-dimensionally divided by a large number of microscopic lens elements forming the microlens array 16, to form a secondary light source (surface light source) on a pupil plane (illumination pupil plane IPP) of the illumination optical system ILS which is a rear focal plane of each lens element.

As an example, the diffractive optical element 10A is provided for normal illumination, the diffractive optical element 10B is for small σ illumination to generate illumination light with a small coherence factor (σ value), and other diffractive optical elements (not shown) are also provided for dipolar illumination, for quadrupolar illumination, for annular illumination, and so on. A spatial light modulator having an array of a large number of microscopic mirrors an inclination angle of each of which is variable, may be used instead of the plurality of diffractive optical elements 10A, 10B, etc., and a fly's eye lens or the like can also be used instead of the microlens array 16.

The illumination light IL from the secondary light source formed on the illumination pupil plane IPP travels via a first relay lens 18, a field stop 20, a mirror 8B to bend the optical path into the −Z-direction, a second relay lens 22, a condenser optical system 24, and a mirror 8C, to be incident at an average incidence angle α in the θx direction onto the illumination target surface (a surface where a designed transfer pattern is arranged) parallel to the XY plane. In other words, the optical axis AXI of the illumination optical system ILS intersects at the incidence angle α in the θx direction with the illumination target surface. The incidence angle α is, for example, from several deg (°) to several ten deg. In a power-off condition, reflective surfaces of the large number of mirror elements 30 arranged in the two-dimensional array pattern in the spatial light modulator 28 are arranged on or near the illumination target surface. The illumination optical system ILS is constructed including the optical members from the beam expander 4 to the condenser optical system 24 and the mirror 8C. The illumination light IL from the illumination optical system ILS illuminates a rectangular illumination region 26A elongated in the X-direction on the array of the large number of mirror elements 30 in the spatial light modulator 28, with a substantially uniform illuminance distribution. The large number of mirror elements 30 are arranged at predetermined pitches in the X-direction and in the Y-direction in a rectangular region including the illumination region 26A. The illumination optical system ILS is supported on a frame not shown.

Figure 2A:
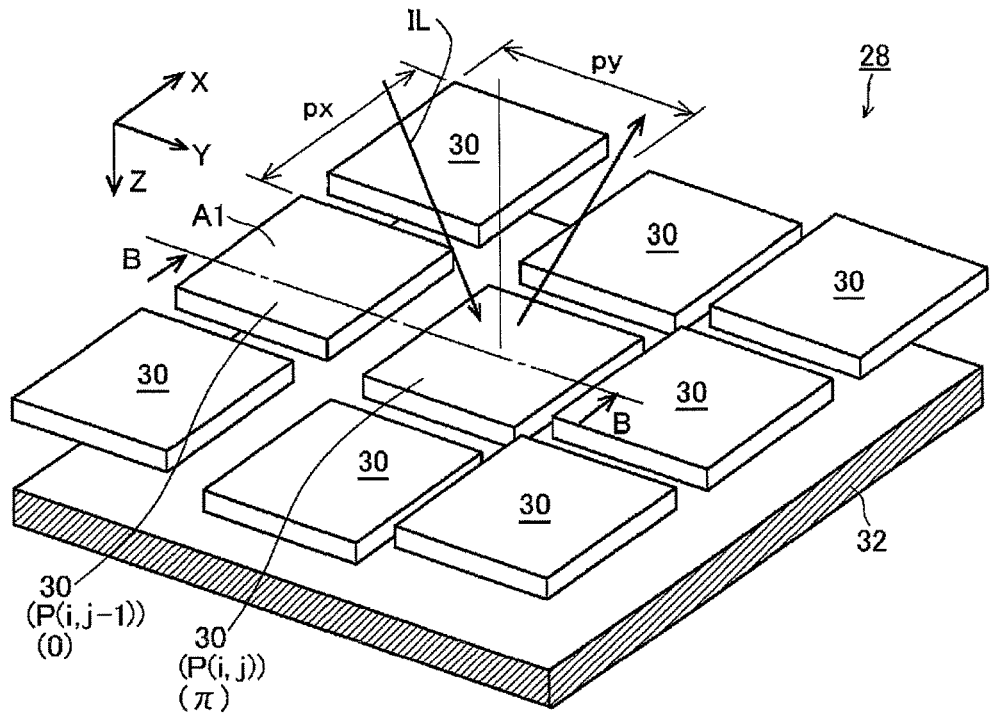
FIG. 2A is an enlarged perspective view showing a part of spatial light modulator 28 in FIG. 1.
Figure 2B:
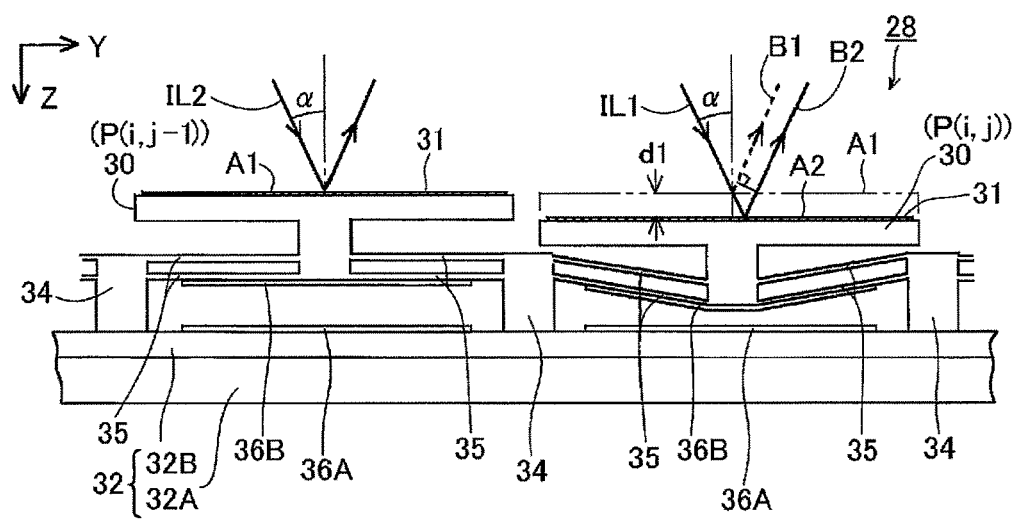
FIG. 2B is a cross-sectional view along the line BB in FIG. 2A.

FIG. 2A is an enlarged perspective view showing a part of a reflective surface of the spatial light modulator 28 in FIG. 1, and FIG. 2B a cross-sectional view along the line BB in FIG. 2A. In FIG. 2A, the large number of mirror elements 30 are arranged at the pitches (periods) px and py in the X-direction and in the Y-direction, respectively, on the reflective surface of the spatial light modulator 28. The X-directional and Y-directional widths of the mirror elements 30 can be assumed to be nearly equal to the pitches px and py, respectively. As an example, the mirror elements 30 are square and the pitches px, py are equal to each other. It is noted herein that the mirror elements 30 may have a rectangular shape or other shape and the pitches px, py may be different from each other.

On the reflective surface, each of the mirror elements 30 is located at a position P(i, j) which is the ith position (i=1, 2, . . . , I) in the X-direction and the jth position (j=1, 2, . . . , J) in the Y-direction. As an example, the number J of mirror elements 30 arranged in the Y-direction (direction corresponding to the scanning direction of the wafer W) is from several hundred to several thousand, and the number I of mirror elements 30 arranged in the X-direction is from several to several ten times the number J. Furthermore, the pitch px (=py) of arrangement of the mirror elements 30 is, for example, approximately from 10 μm to 1 μm. The spatial light modulator 28 has the large number of mirror elements 30, and a base member 32 which supports each of the mirror elements 30 through hinge portions 35 (cf. FIG. 2B) each with flexibility (elasticity).

In FIG. 2B, the base member 32 is composed of a substrate 32A of a flat plate shape which is, for example, comprised of silicon, and an insulating layer 32B of silicon nitride (e.g., $Si_3N_4$) or the like formed on a surface of the substrate 32A. Support portions 34 are formed at predetermined pitches in the X-direction and in the Y-direction on the surface of the base member 32 and a back-side projection of each mirror element 30 is supported through a pair of two-stage hinge portions 35 with flexibility in the Z-direction by elastic deformation, between adjacent Y-directional support portions 34. The support portions 34, hinge portions 35, and mirror elements 30 are integrally formed, for example, of polysilicon. A reflective film 31 comprised of a thin film of metal (e.g., aluminum or the like) to enhance reflectivity is formed on the reflective surface (front surface) of each mirror element 30.

Furthermore, electrodes 36A are formed on the surface of the base member 32 on the bottom side of mirror elements 30 and electrodes 36B are formed on the respective bottom faces of the hinge portions 35 so as to be opposed to the electrodes 36A. Signal lines (not shown) for applying a predetermined voltage between corresponding electrodes 36A, 36B for each mirror element 30 are provided in a matrix on the surface of the base member 32 and on the side faces of the support portions 34. In this case, in a power-off condition or in a power-on condition without application of the voltage between the electrodes 36A, 36B (first state), the reflective surface of the mirror element 30 agrees with a reference plane A1 which is a plane parallel to the XY plane, as indicated by the mirror element 30 at the position P(i, j−1). On the other hand, in the power-on condition with application of the predetermined voltage between the electrodes 36A, 36B (second state), the reflective surface of the mirror element 30 agrees with a plane A2 displaced by a distance d1 in the Z-direction from the reference plane A1 in parallel with the XY plane, as indicated by the mirror element 30 at the position P(i, j) where the illumination light IL1 is incident. The modulation control unit 48 in FIG. 1 controls the voltage between the electrodes 36A, 36B for each mirror element 30 at the position P(i, j), in accordance with information of the phase distribution (uneven pattern) of the illumination light IL set from the main control system 40. Each mirror element 30 is set either in the first state or in the second state.

The spatial light modulator 28 of this microscopic three-dimensional structure can be manufactured by use of the MEMS (Microelectromechanical Systems) technology, for example, as described in Non Patent Literature 1 cited in the Background Art. Since each mirror element 30 of the spatial light modulator 28 needs only to be set in the first state or in the second state by parallel displacement, it is easy to achieve downsizing of the mirror elements 30 and increase in the number of arrangement of mirror elements 30.

In the state in which the reflective surface of each mirror element 30 agrees with the reference plane A1 (the first state), let us define a change amount of the phase of the illumination light IL reflected by the mirror element 30, as a first phase δ1; in the present embodiment the phase δ1 is 0°. In the state in which the reflective surface of each mirror element 30 agrees with the plane A2 displaced by the distance d1 from the reference plane A1 (the second state), let us define a change amount of the phase of the illumination light IL reflected by the mirror element 30, as a second phase δ2; the phase δ2 is different by 180° (π (rad)) from the phase δ1. Namely, the relations below hold. It is, however, noted that an error of several deg (°) or so from the below formula is permitted for the phase δ2, with consideration to manufacturing error of the spatial light modulator 28, driving error by the modulation control unit 48, and so on.

$$\delta 1 = 0° \tag{1A}$$

$$\delta 2 = 180° = \pi(rad) \tag{1B}$$

In the description hereinafter the phases without unit refer to phases in rad. The second phase δ2 is a difference between the change amount of the phase of the wavefront of reflected light B1 indicated by a dotted line in the state in which the reflective face of the mirror element 30 at the position P(i, j) agrees with the reference plane A1 and the change amount of the phase of the wavefront of reflected light B2 in the state in which the reflective face agrees with the plane A2 at the distance d1. As an example, when the incidence angle α is assumed to be 0° and the wavelength of the illumination light IL1 entering the reflective face of the mirror element 30 is represented by λ (λ=193 nm herein), the distance d1 is given as follows.

$$d1 = \lambda/4 \tag{2}$$

In FIG. 2A, each of the mirror elements 30 of the spatial light modulator 28 is controlled into the first state in which the mirror element 30 reflects the illumination light IL incident thereto with the phase change of 0° or into the second state in which the mirror element 30 reflects the illumination light IL incident thereto with the phase change of 180°. In the description hereinafter, the mirror element 30 set in the first state will also be referred to as a mirror element of phase 0 and the mirror element 30 set in the second state as a mirror element of phase π.

As an example, at every emission of a predetermined number of pulses of the illumination light IL, the main control system 40 supplies information of a phase distribution (uneven pattern) of the illumination light IL set by the spatial light modulator 28, to the modulation control unit 48. In accordance therewith, the modulation control unit 48 controls each of the mirror elements 30 of the spatial light modulator 28 into the phase 0 or into the phase π. A spatial image according to the phase distribution is formed on the surface of the wafer W.

In FIG. 1, the base member 32 of the spatial light modulator 28 is supported on a frame FL, for example, by support members 56 arranged at three positions which are not aligned on an identical straight line (among which the third support member is not shown), and by nuts 57. Furthermore, the back surface opposed to the reflective surface of the base member 32 (the reflective surface of the array of mirror elements 30) is coupled to the frame FL through bolts 58 and nuts 57 at a plurality of positions. In this case, the flatness of the reflective surface of the spatial light modulator 28 can be adjusted by adjusting a stress distribution on the back surface of the base member 32 through adjustment of positions of nuts 57 at two locations in the axial direction of the bolts 58.

The illumination light IL, after reflected by the array of many mirror elements 30 in the illumination region 26A of the spatial light modulator 28, is incident at the average incidence angle α into the projection optical system PL. The projection optical system PL with the optical axis AXW supported by an unrepresented column is a reduction projection optical system which is non-telecentric on the spatial light modulator 28 (object plane) side and telecentric on the wafer W (image plane) side. The projection optical system PL forms a demagnified image of the spatial image according to the phase distribution of the illumination light IL set by the spatial light modulator 28, on an exposure region 26B (which is a region optically conjugate with the illumination region 26A) in one shot area on the wafer W. A projection magnification β of the projection optical system PL is, for example, approximately from ⅒ to 1/100. When it is assumed that the numerical aperture on the image plane side of the projection optical system PL is NA, the wavelength of the illumination light IL is λ, and the illumination condition is normal illumination, the resolution Re of the projection optical system PL (the resolution limit expressed by a line width of a periodic pattern) is given as follows.

$$Re = \lambda/(2 \cdot NA) \tag{3}$$

In the present embodiment, the resolution Re is set to be larger than the width (β·py) of the image of the mirror element 30 of the spatial light modulator 28. As an example, the resolution Re is about double the width of the image of the mirror element 30. For example, when the size of the mirror element 30 (pitch of the array) is approximately several μm and the projection magnification β of the projection optical system PL is about 1/100, the resolution Re is approximately double of several ten nm. Since the projection optical system PL has an aperture stop (not shown), the resolution of the projection optical system PL in an below-described inspection of the spatial light modulator 28 may be set to be lower than the resolution in the exposure, by the aperture stop.

The wafer W (substrate) includes, for example, one obtained by coating a surface of a base material of a circular flat plate shape of silicon or SOI (silicon on insulator), with a photoresist (photosensitive material) in the thickness of about several ten nm to 200 nm.

With the use of the projection optical system PL non-telecentric on the object side as in the present embodiment, the reflective surfaces of the large number of mirror elements 30 in the spatial light modulator 28 and the exposure surface of the wafer W (the surface of the photoresist) can be arranged approximately in parallel to each other. Therefore, it is easy to design and manufacture the exposure apparatus.

When the exposure apparatus EX is of a liquid immersion type, it is provided with a local liquid immersion apparatus to supply and collect a liquid (e.g., pure water) which transmits the illumination light IL, between an optical member at the tip of the projection optical system PL and the wafer W, for example, as disclosed in U.S. Pat. Published Application No. 2007/242247. The resolution can be further increased in the case of the liquid immersion type because the numerical aperture NA can be set larger than 1.

In FIG. 1, the wafer W is sucked and held on the top surface of the wafer stage WST through a wafer holder (not shown) and the wafer stage WST is configured to implement step movement in the X-direction and Y-direction on an unillustrated guide surface and movement at a constant speed in the Y-direction. X-directional and Y-directional positions, an angle of rotation in the θz direction, etc. of the wafer stage WST are measured by a laser interferometer 45 and this measurement information is supplied to a stage control system 44. The stage control system 44 controls the position and speed of the wafer stage WST through a driving system 46 such as a linear motor, based on the control information from the main control system 40 and the measurement information from the laser interferometer 45. The apparatus is also provided with an alignment system (not shown) to detect positions of alignment marks on the wafer W, for carrying out alignment of the wafer W.

A spatial image measuring apparatus 54 for measuring an intensity distribution of a spatial image formed in the exposure region 26B is provided in the vicinity of the wafer W in the upper part of the wafer stage WST. The spatial image measuring apparatus 54 has, as an example, an enlarging optical system for enlarging the spatial image and a two-dimensional image pickup device for taking the enlarged spatial image. A detection signal output from the spatial image measuring apparatus 54 is supplied to an arithmetic apparatus 55 and the arithmetic apparatus 55 processes the detection signal to obtain a characteristic of the spatial light modulator 28 as described below and supplies the obtained characteristic to the main control system 40. Input/output apparatuses (not shown) for input/output of various types of information are also connected to the main control system 40. The inspection apparatus 53 for the spatial light modulator 28 is configured including the illumination optical system ILS, modulation control unit 48, projection optical system PL, spatial image measuring apparatus 54, and arithmetic apparatus 55. The spatial image measuring apparatus 54 to be used herein can also be a scan-type measuring apparatus including a pinhole, a condensing optical system for condensing light incident into the pinhole, and a photoelectric detector for receiving the condensed light.

In exposure of the wafer W, the alignment of the wafer W is first carried out and thereafter the illumination condition of the illumination optical system ILS is set, as basic operation. Furthermore, the main control system 40 supplies to the modulation control unit 48, information of a phase distribution corresponding to a pattern to be exposed in each shot area on the wafer W. Then the wafer W is positioned at a scan start position, for example, for carrying out exposure in shot areas SA21, SA22, . . . aligned on a line in the Y-direction on the surface of the wafer W shown in FIG. 3A. Thereafter, scan is started at a constant speed in the +Y-direction on the wafer W. Arrows in the shot area SA21 and other areas in FIG. 3A indicate directions of movement of the exposure region 26B relative to the wafer W.

Next, the main control system 40 supplies to the modulation control unit 48, the information of the relative position of the shot area SA21 on the wafer W to the exposure region 26B and the modulation control unit 48 reads out a partial phase distribution as a transfer target in accordance with the relative position and sets the read partial phase distribution in the spatial light modulator 28. Then the main control system 40 supplies the emission trigger pulses TP to the power supply 42, whereby the exposure region 26B on the wafer W is exposed with the target spatial image according to the position in the Y-direction. This operation is repeatedly carried out every time the wafer W has moved by a predetermined amount and before the shot area SA21 has crossed the exposure region 26B.

Thereafter, for exposure of the shot area SA22 adjacent to the shot area SA21 on the wafer W, while the wafer W is kept scanned in the same direction, the main control system 40 supplies the information of the relative position of the shot area SA22 to the exposure region 26B to the modulation control unit 48 and supplies the emission trigger pulses TP to the power supply 42. In this manner, the exposure can be continuously carried out from the shot area SA21 to SA22 in the maskless method. Then, supposing the exposure is shifted to a line including the adjacent shot areas SA31, SA32 in the X-direction on the wafer W in FIG. 3A, the wafer stage WST is actuated to implement step movement of the wafer W in the X-direction (non-scanning direction perpendicular to the scanning direction). Then, the scanning direction of the wafer W relative to the exposure region 26B indicated by a dotted line is set to the opposite −Y-direction, and the main control system 40 supplies the information of the relative position of the shot area SA31 or the like to the exposure region 26B to the modulation control unit 48 and supplies the emission trigger pulses TP to the power supply 42. By this, the exposure can be continuously carried out from the shot area SA32 to SA31. In this exposure, it is also possible to implement exposure of mutually different spatial images in the shot areas SA21, SA22, and so on. Thereafter, the photoresist of the wafer W is developed to form a resist pattern corresponding to a circuit pattern in each shot area on the wafer W.

Next, a method for specifying a defective element among the mirror elements 30 of the spatial light modulator 28 will be described as an example of the method for inspecting the spatial light modulator 28 in the exposure apparatus EX of the present embodiment, with reference to the flowchart of FIG. 7. A defective element refers to such a mirror element 30 that even if the modulation control unit 48 preforms control to bring it into the first state (phase 0) or into the second state (phase π), it cannot be set in the first state or in the second state, respectively. This inspection method is executed under control of the main control system 40.

Figure 4A:
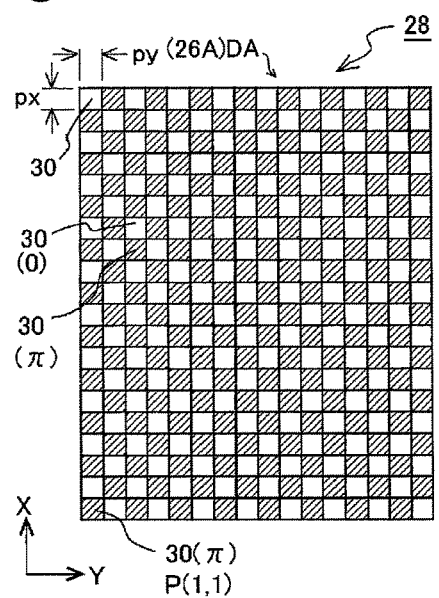
FIG. 4A is a partially enlarged view showing a first phase distribution of a checkered pattern set by the spatial light modulator 28, FIG. 4B an enlarged view showing a spatial image corresponding to the phase distribution of FIG. 4A, and FIG. 4C a drawing showing an intensity distribution on the line CC in FIG. 4B.
Figure 7:
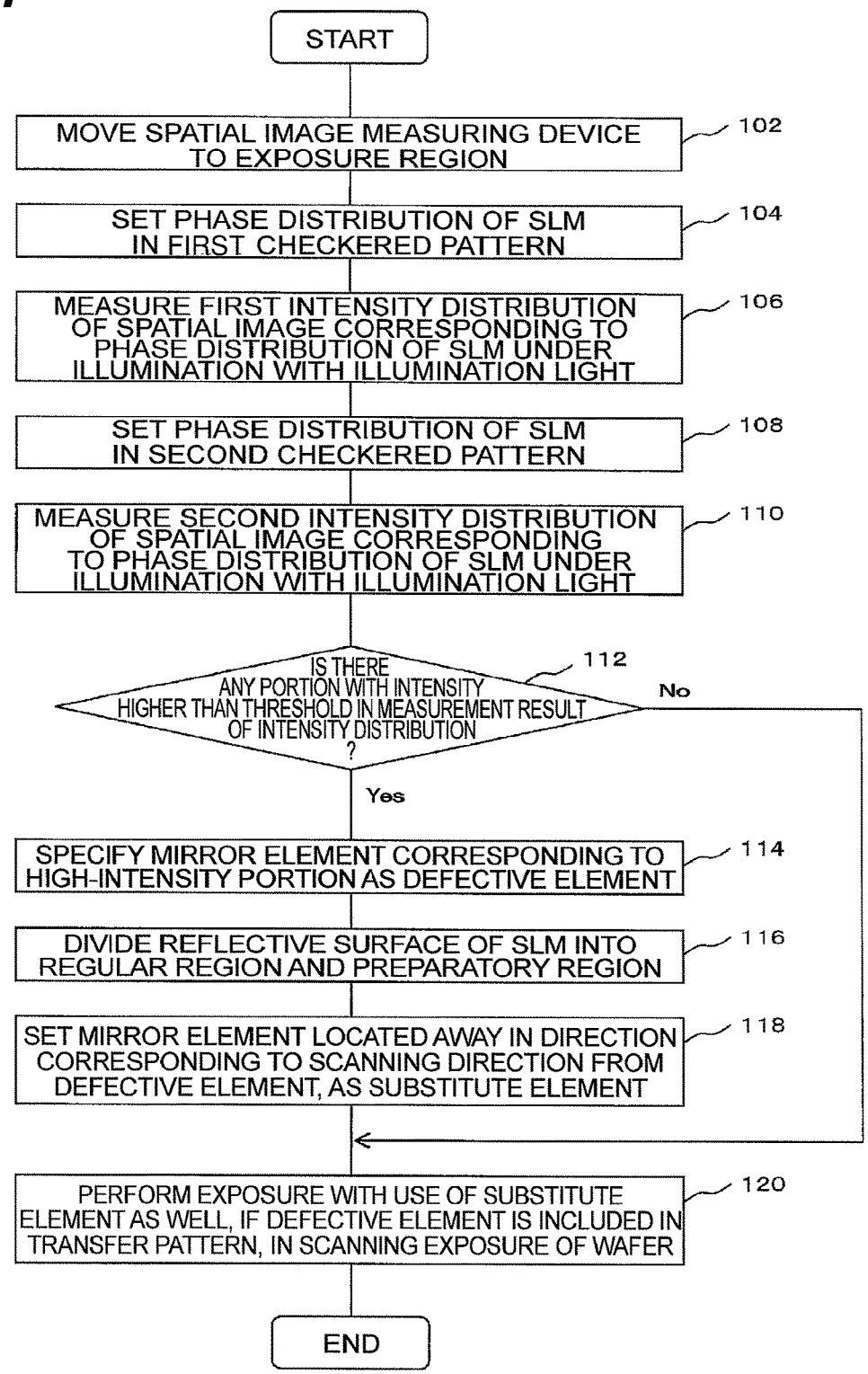
FIG. 7 is a flowchart showing an inspection method in the first embodiment.

First, in step 102 in FIG. 7, the wafer stage WST is driven to move a light receiving surface of the spatial image measuring apparatus 54 to a position where it covers the exposure region 26B (which is not illuminated yet with the illumination light IL in this stage). Furthermore, the illumination condition of the illumination optical system ILS is small σ illumination with the σ value of about 0.1, as an example, and the polarization condition is set to unpolarized light. In next step 104, as shown in FIG. 4A, an inspection target area DA is defined as a portion where the illumination region 26A is set in the array of mirror elements 30 of the spatial light modulator 28. Then, in accordance with the control information from the main control system 40, the modulation control unit 48 drives each of the mirror elements 30 so that the mirror elements 30 in the first state (phase 0) and the mirror elements 30 in the second state (phase π) are arrayed in a first checkered pattern in the inspection target area DA.

The array in the checkered pattern means that in the case where among the first-line mirror elements 30 parallel to the X-axis in the inspection target area DA, the odd-numbered mirror elements 30 including one at the position P(1, 1) are in the second state (phase π) while the even-numbered mirror elements 30 are in the first state (phase 0), the second-line mirror elements 30 include the odd-numbered mirror elements 30 with the phase 0 and the even-numbered mirror elements 30 with the phase π and the following lines are repetitions of the same arrays as in the first line and the second line. The checkered pattern is also called a checker pattern or checkerboard pattern (Checkerboard Pattern)). Furthermore, the checkered pattern where the mirror element 30 at the position P(1, 1) has the phase π, like the array in FIG. 4A, is called the first checkered pattern in the present embodiment.

Figure 4B:
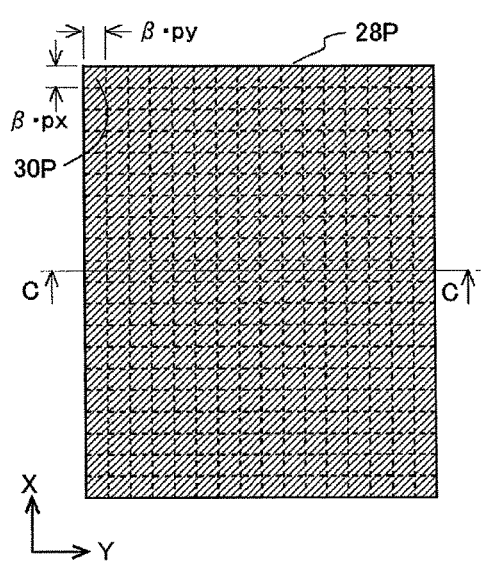

In next step 106, the main control system 40 supplies the emission trigger pulses TP to the power supply 42 to illuminate the illumination region 26A in the array of mirror elements 30 with the illumination light IL, whereby a spatial image 28P in FIG. 4B (which is shown as an enlarged image) corresponding to the phase distribution in FIG. 4A is formed in the exposure region 26B via the projection optical system PL. For convenience of explanation, the spatial image 28P is illustrated as an erect image. Then the spatial image measuring apparatus 54 measures an intensity distribution in the X-direction and Y-direction of the spatial image 28P and the arithmetic apparatus 55 takes in the measured image data.

Figure 5A:
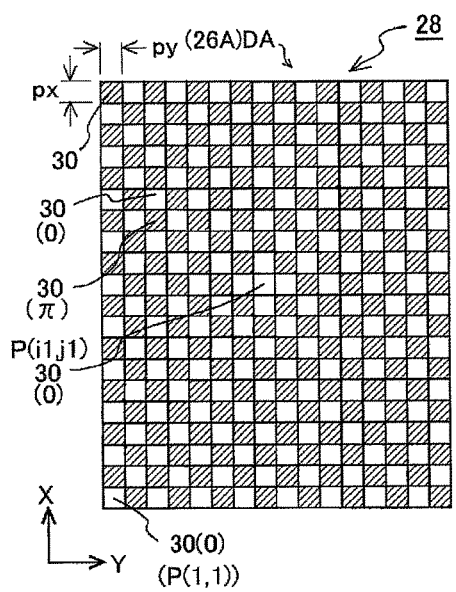
FIG. 5A is a partially enlarged view showing a second phase distribution of a checkered pattern set by the spatial light modulator 28, FIG. 5B an enlarged view showing a spatial image including a defective part corresponding to the phase distribution of FIG. 5A, and FIG. 5C a drawing showing an intensity distribution on the line CC in FIG. 5B.
Figure 5B:
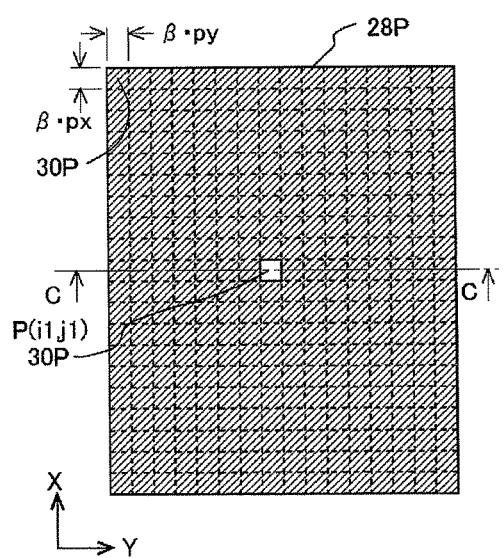

In next step 108, in accordance with the control information from the main control system 40, the modulation control unit 48 drives each of the mirror elements 30 so that the mirror elements 30 in the first state (phase 0) and the mirror elements 30 in the second state (phase π) are arrayed in a second checkered pattern shown in FIG. 5A, in the inspection target area DA. The second checkered pattern is an array obtained by interchanging the phase-0 portions and the phase-π portions in the first checkered pattern with each other, in which the mirror element 30 at the position P(1, 1) in FIG. 5A has the phase 0. In next step 110, the illumination region 26A is illuminated with the illumination light IL, whereby a spatial image 28P in FIG. 5B corresponding to the phase distribution in FIG. 5A is formed in the exposure region 26B via the projection optical system PL. Then the spatial image measuring apparatus 54 measures an intensity distribution of the spatial image 28P and the arithmetic apparatus 55 takes in the measured image data.

Figure 4C:
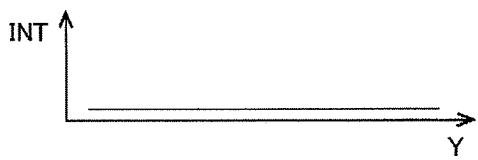

In next step 112, the arithmetic apparatus 55 sequentially processes the image data (intensity distributions) of the spatial images 28P measured in steps 106 and 110 to detect a portion with the intensity higher than a predetermined threshold. In this case, in the array of the first checkered pattern in FIG. 4A the states of all the mirror elements 30 are the set states and the resolution of the projection optical system PL is larger (or coarser) than the width of the image of the mirror element 30. For this reason, the spatial image 28P in FIG. 4B has a low level throughout the entire surface and an intensity profile INT along the line CC in FIG. 4B (which is a straight line passing centers of virtual images of the mirror elements 30 near the center and being parallel to the Y-axis) is at a substantially constant low level as shown in FIG. 4C.

Figure 5C:
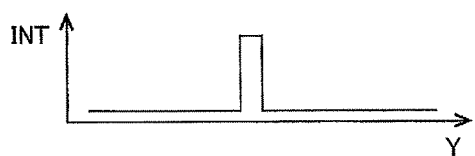

On the other hand, in the array of the second checkered pattern in FIG. 5A, the state (phase 0) of the mirror element 30 at the position P(i1, j1) (i1=11 and j1=8 as an example) is different from the set state (phase π). At this time, the widths of images of three mirror elements 30 in the X-direction and three mirror elements 30 in the Y-direction around the center at the position P(i1, j1) are three times the width of the image of one mirror element 30 and thus an image of a portion including the mirror element 30 at the position P(i1, j1) is resolved by the projection optical system PL. For this reason, the spatial image 28P in FIG. 5B has a high level in a portion of a virtual image 30P of the mirror element 30 at the position P(i1, j1) and a low level in the other portions. Therefore, an intensity profile INT along the line CC in FIG. 5B (a straight line passing the center of the image 30P and being parallel to the Y-axis) is at the high level in the portion corresponding to the image 30P, as shown in FIG. 5C. In this case, the threshold in step 112 is set at a middle point between the low level and the high level of the intensity profile INT in FIG. 5C (e.g., which are levels preliminarily determined by measurement). For this reason, the arithmetic apparatus 55 can detect the portion of the image 30P as a portion with the intensity higher than the threshold. If there is no portion with the intensity higher than the threshold, the operation moves to step 120.

Since at this point the intensity of the portion of image 30P is higher than the threshold, the operation goes to step 114. Then the arithmetic apparatus 55 specifies the mirror element 30 at the position P(i1, j1) in the spatial light modulator 28 corresponding to the portion (image 30P) with the intensity higher than the threshold in the spatial image 28P, as a defective element 38 (cf. FIG. 6A). The information of the position of the defective element 38 is supplied from the main control system 40 to the modulation control unit 48.

Figure 6A:
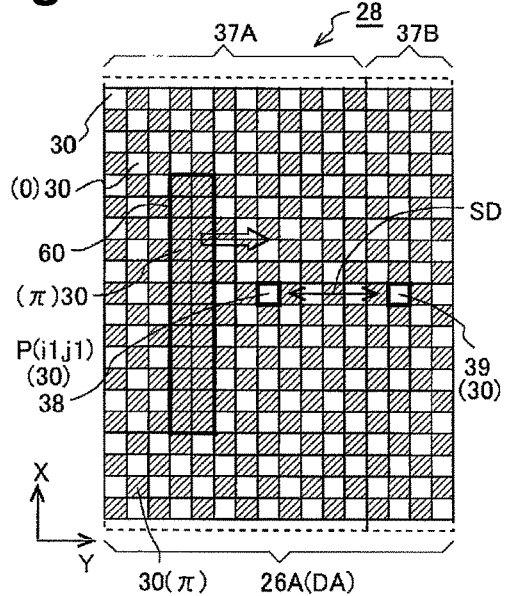
FIG. 6A, FIG. 6B, FIG. 6C, and FIG. 6D are respective partially enlarged views showing states of Y-directional movement of a rectangular pattern region in a phase distribution formed by the spatial light modulator 28.

In next step 116, the modulation control unit 48, as shown in FIG. 6A, divides the inspection target area DA (illumination region 26A) in the array of mirror elements 30 into a regular region 37A including the defective element 38 and a preparatory region 37B consisting of multiple lines (four lines in FIG. 6A) in the Y-direction not including the defective element, in the Y-direction (direction SD corresponding to the scanning direction on the wafer W). The preparatory region 37B is a region narrower than the regular region 37A. In next step 118, the modulation control unit 48 sets and stores the mirror element 30 located away in the direction SD from the defective element 38 in the preparatory region 37B, as a substitute element 39 (preparatory element).

Thereafter, in an exposure step of step 120, when the phase distribution of the array of mirror elements 30 corresponding to the spatial image formed on the surface of the wafer W includes the portion set in the phase π by the defective element 38, the modulation control unit 48 uses the substitute element 39 in place of the defective element 38. As an example, let us assume that a spatial image corresponding to a phase distribution in which the phases of all the mirror elements 30 in a pattern region 60 elongated in the X-direction in FIG. 6A are π is formed on the surface of the wafer W. At this time, the phase distribution of the mirror elements 30 in the part other than the pattern region 60 is such that the mirror elements 30 of phase 0 and the mirror elements 30 of phase π are set in a checkered pattern, and the spatial image in the part other than the pattern region 60 is at the low level. In the preparatory region 37B, normally, the mirror elements 30 of phase 0 and the mirror elements 30 of phase π are set in a checkered pattern, the substitute element 39 is set in the phase 0, and the spatial image in the portion of the preparatory region 37B is at the low level.

Figure 6B:
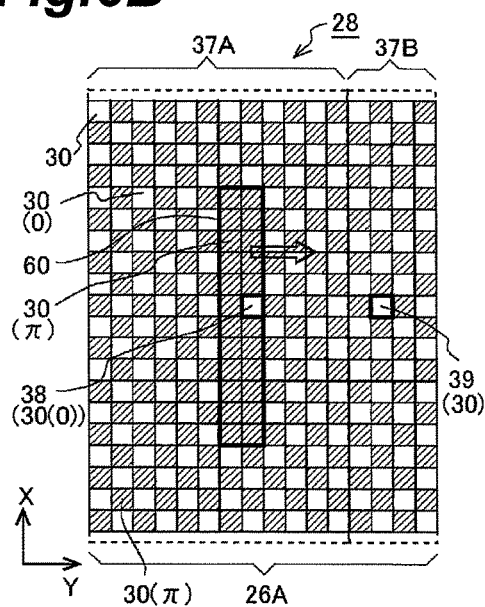
Figure 6C:
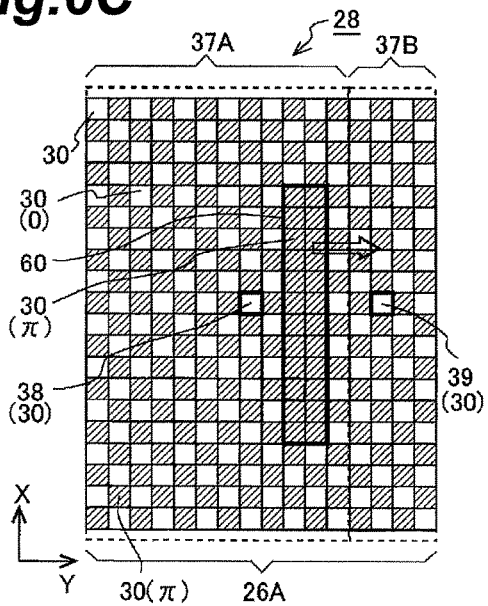
Figure 6D:
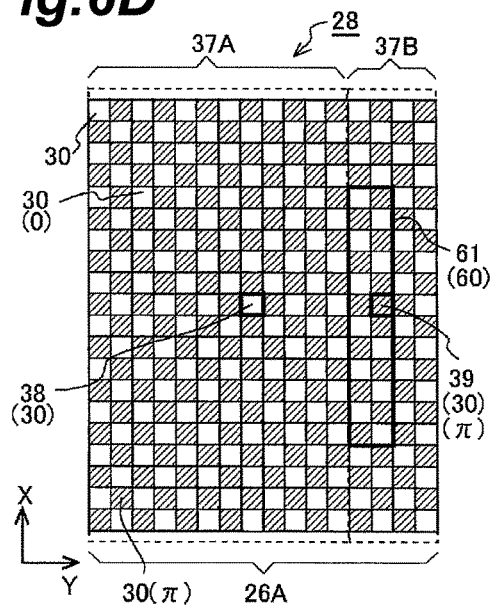

In this case, during the scanning exposure, the entire illumination region 26A is illuminated pulsatively with the illumination light IL and the pattern region 60 also moves gradually in the Y-direction in synchronism with gradual Y-directional scan of the wafer W. Then, since the phase of the defective element 38 is 0 in the state in which the defective element 38 is included in the pattern region 60, as shown in FIG. 6B, an exposure amount decreases on the surface of the wafer W corresponding to that portion. Thereafter, as shown in FIG. 6C, the pattern region 60 passes over the defective element 38 and then, as shown in FIG. 6D, the pattern region 60 reaches a region 61 including the substitute element 39 in the preparatory region 37B, whereupon the modulation control unit 48 sets the phase of the substitute element 39 to π. At this time, an exposure amount on the wafer W by the image of the portion including the substitute element 39 is set so as to cancel out the exposure amount decreased by the defective element 38. This ensures evenness of exposure amounts on the surface of the wafer W, even with occurrence of the defective element 38, and allows the spatial image corresponding to the pattern region 60 to be accurately formed on the surface of the wafer W. Therefore, the target pattern can be highly accurately formed by development of the photoresist of the wafer W.

If the defective element 38 appears in the preparatory region 37B, the Y-directional width of the illumination region 26A may be set so as not to include the defective element, for example, by the field stop 20, as an example. The number of defective element 38 may be two or more and one substitute element 38 can substitute for a plurality of defective elements.

The effects and others of the present embodiment are as described below.

(1) The exposure apparatus EX of the present embodiment has the spatial light modulator 28 having the array of mirror elements 30 (optical elements). The method for inspecting the spatial light modulator 28 includes: steps 104, 108 of performing such control that the mirror elements 30 in the first state which reflect incident light with the phase change of the first phase (0°) and the mirror elements 30 in the second state which reflect incident light with the phase change of the second phase (180°) are arrayed in the checkered pattern, in the inspection target area DA in the array of mirror elements 30; steps 106, 110 of guiding the light having passed the inspection target area DA, to the projection optical system PL with the resolution limit coarser than the width of the image of one mirror element 30, to form the spatial image; and steps 112, 114 of inspecting the characteristic of the spatial light modulator 28 from the spatial image formed by the projection optical system PL.

The inspection apparatus 53 for the spatial light modulator 28 has: the illumination optical system ILS which illuminates the inspection target area DA in the array of mirror elements 30; the modulation control unit 48 (control apparatus) which performs such control that the mirror elements 30 in the first state and the mirror elements 30 in the second state are arrayed in the checkered pattern, in the inspection target area DA; the projection optical system PL which forms the spatial image from the light having passed the inspection target area DA; and the arithmetic apparatus 55 which performs the inspection of the spatial light modulator 28, based on the spatial image formed by the projection optical system PL.

According to the present embodiment, the mirror elements 30 in the first state and the mirror elements 30 in the second state are arrayed in the checkered pattern, in the inspection target area DA in the array of mirror elements 30 of the spatial light modulator 28 and the light from the inspection target area DA is guided to the projection optical system PL with the resolution limit coarser than the width of the image of one mirror element to form the spatial image, whereby if there is a difference between the characteristic of the array of mirror elements 30 and a target characteristic the spatial image changes from the substantially constant low-level state. Therefore, the inspection of the characteristic of the spatial light modulator 28 can be readily performed in an on-body condition with the use of the spatial image.

(2) Since the present embodiment is configured to inspect the presence/absence of the defective element 38 among the mirror elements 30, as the characteristic of the spatial light modulator 28, it is feasible to prevent the pattern formed on the wafer W from having a shape error due to the existence of the defective element 38. The present embodiment is configured to assign the substitute element 39 in the presence of the defective element 38, but the spatial light modulator 28 may be replaced with another in the presence of the defective element 38. In this case, the main control system 40 of the exposure apparatus EX may be configured to make a warning urging replacement of the spatial light modulator, displayed on a display part (monitor) provided on a console of the exposure apparatus EX. The apparatus may also be configured to display attention information of assignment of the substitute element on the display part, on the occasion of assigning the substitute element 39 in the presence of the defective element 38. The foregoing warning or attention information may be one sent to a master computer system having a management function for many lithography units in a manufacturing plant.

(3) Since the spatial light modulator 28 has the mirror elements 30 (reflective elements) as optical elements, it has high utilization efficiency of illumination light IL. However, it is also possible to use a transmission type spatial light modulator in which each of individual optical elements changes the phase of transmitted light by the predetermined phase change φ1 or (φ1+180°), instead of the spatial light modulator 28. Such optical elements to be used herein can be electro-optic devices changing the refractive index depending upon voltage, liquid crystal cells, or the like.

(4) The exposure method by the exposure apparatus EX in the present embodiment is the exposure method for exposing the wafer W (substrate) with the illumination light IL (exposure light) via the spatial light modulator 28 having the array of mirror elements 30 and via the projection optical system PL, the exposure method including the step of performing the inspection of the spatial light modulator 28 by the aforementioned method for inspecting the spatial light modulator 28.

The exposure apparatus EX of the present embodiment is the exposure apparatus for exposing the wafer W with the illumination light IL (exposure light) from the illumination optical system ILS (illumination system) via the projection optical system PL (projection system), the exposure apparatus having: the spatial light modulator 28 which is arranged on the object plane side of the projection optical system PL and which has the array of mirror elements 30 each of which can be controlled so as to guide the illumination light IL to the projection optical system PL; and the above-described inspection apparatus 53 for the spatial light modulator.

According to the exposure method or the exposure apparatus EX, a variety of patterns can be formed on the surface of the wafer W in the maskless method through the use of the spatial light modulator 28. Furthermore, since the inspection of the characteristic of the spatial light modulator 28 can be readily performed in the on-body condition, reduction of throughput of the exposure step can be suppressed on the occasion of performing the inspection of the characteristic of the spatial light modulator 28.

Furthermore, the illumination optical system ILS and the projection optical system PL of the exposure apparatus EX also serve as the illumination optical system ILS and the projection optical system PL of the inspection apparatus 53. Therefore, the configuration of the inspection apparatus 53 is simple. At least one of the illumination apparatus and the projection optical system of the inspection apparatus 53 may be detachably provided separately from the illumination optical system ILS and the projection optical system PL. The inspection apparatus 53 may be provided as a dedicated inspection apparatus for the spatial light modulator 28, independently of the exposure apparatus EX.

(5) The illumination light IL from the illumination optical system ILS is obliquely incident nearly at the incidence angle α to the mirror elements 30 (reflective elements) and the reflected light from the mirror elements 30 is incident to the projection optical system PL so as to intersect the optical axis AXW of the projection optical system PL. Therefore, since the projection optical system PL is non-telecentric on the object plane side, the whole reflected light from the spatial light modulator 28 can be guided via the projection optical system Pl onto the wafer W, achieving high utilization efficiency of the illumination light IL. Furthermore, the polarization state of the illumination light IL set by the polarization control optical system 6 can be accurately reproduced on the surface of the wafer W.

Second Embodiment

Figure 8A:
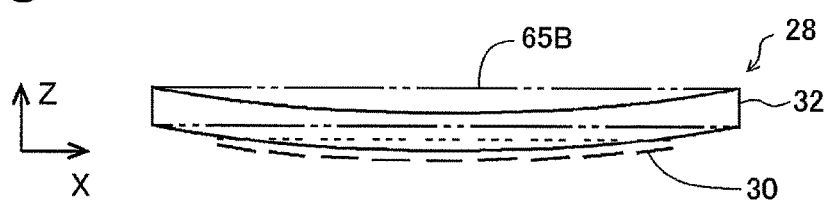
FIG. 8A is an enlarged view showing an example of curvature of a reflective surface of the spatial light modulator 28, in the second embodiment.

Next, the second embodiment will be described with reference to FIGS. 1 and 8A to 8B. The present embodiment also uses the exposure apparatus EX in FIG. 1 but is different in that flatness of the reflective surface is inspected as a characteristic of the spatial light modulator 28. In conjunction therewith, the operation of the arithmetic apparatus 55 is different from that in the first embodiment.

In the inspection of the characteristic of the spatial light modulator 28 in the present embodiment, the same operation as in steps 102, 104, and 106 in FIG. 7 is carried out. Namely, the array in the illumination region 26A of the mirror elements 30 of the spatial light modulator 28 is arranged so that the mirror elements 30 of phase 0 and the mirror elements 30 of phase π are arrayed in the checkered pattern, as shown in FIG. 4A, and the spatial image measuring apparatus 54 measures the intensity distribution of the spatial image corresponding to the phase distribution of FIG. 4A.

Figure 8B:
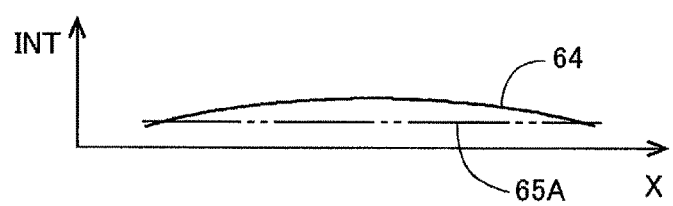
FIG. 8B is a drawing showing an example of intensity distribution of a spatial image.

An intensity profile 64 indicated by a solid line in FIG. 8B is an intensity profile INT of a portion along a straight line parallel to the X-axis in the spatial image measured by the spatial image measuring apparatus 54. In practice, intensity profiles are measured along a plurality of straight lines parallel to the X-axis, which are arranged at predetermined intervals in the Y-direction on the entire surface of the spatial image, and the measurement result is supplied to the arithmetic apparatus 55. In the present embodiment, information of relationship between intensity profiles INT of spatial images and corresponding curvatures of the reflective surface of the spatial light modulator 28 is preliminarily obtained and this information is stored in a memory in the arithmetic apparatus 55. When the intensity profile 64 including distortion information of the base member 32 is a spherical profile as shown in FIG. 8B as an example, it is assumed that the base member 32 of the spatial light modulator 28 (and, in turn, the reflective surface of the array of mirror elements 30) is curved in a spherical shape, as shown in FIG. 8A. Then, the arithmetic apparatus 55 makes information of the intensity profile 64 and a known intensity profile in the case where the reflective surface of the array of mirror elements 30 is flat (e.g., a flat profile like an intensity profile 65A), displayed, for example, in the form of a two-dimensional image on the unillustrated monitor through the main control system 40.

In response thereto, for example, an operator adjusts the positions of the nuts 57 along the bolts 58 on the back surface of the base member 32 of the spatial light modulator 28 in FIG. 1 to control a stress distribution acting on the base member 32, whereby the flatness of the base member 32 is adjusted so that the intensity profile 64 measured becomes closer to the intensity profile 65A. In this case, it is preferable to execute the operation in steps 104, 106 every adjustment of flatness of the base member 32 to measure the intensity distribution INT of the spatial image. By repeating this operation, the base member 32 of the spatial light modulator 28 and, in turn, the reflective surface of the array of mirror elements 30 can be made flat as indicated by position 65B of chain double-dashed lines.

The exposure apparatus may be configured so that the arithmetic apparatus 55 supplies information of the stress distribution to be added to the base member 32.

The exposure apparatus may also be modified as follows: one or more actuators are provided for varying the stress distribution acting on the base member 32, on the back surface of the base member 32 of the spatial light modulator 28 and the actuators are driven so as to flatten the reflective surface of the array of mirror elements 30, based on information about the flatness of the base member 32 from the arithmetic apparatus 55, information about curvature of the reflective surface of the spatial light modulator 28, or information about light intensity distribution at the position of the spatial image.

In this second embodiment as well, the main control system 40 of the exposure apparatus EX may be configured to make the information about the flatness of the reflective surface of the array of mirror elements 30 displayed on the display part (monitor) provided on the console of the exposure apparatus EX, and the information may be sent to the master computer system. If the above operation results in failure in correcting the reflective surface of the array of mirror elements 30 into a flat surface, information of the failure may be displayed on the display part or may be sent to the master computer system.

Third Embodiment

Next, the third embodiment will be described with reference to FIGS. 1 and 9A to 9D. The present embodiment also uses the exposure apparatus EX in FIG. 1 but is different in that stray light is inspected as a characteristic of the spatial light modulator 28 and flare of the projection optical system PL is inspected (or measured) using the inspection result. In conjunction therewith, the operation of the arithmetic apparatus 55 is different from that in the first embodiment.

In the inspection of the characteristic of the spatial light modulator 28 in the present embodiment, the same operation as in steps 102, 104, and 106 in FIG. 7 is first carried out. Namely, the array in the illumination region 26A of the mirror elements 30 of the spatial light modulator 28 is arranged so that the mirror elements 30 of phase 0 and the mirror elements 30 of phase $\pi$ are arrayed in a checkered pattern as shown in FIG. 9A and the spatial image measuring apparatus 54 measures an intensity distribution of a spatial image corresponding to the phase distribution in FIG. 9A.

Figure 9A:
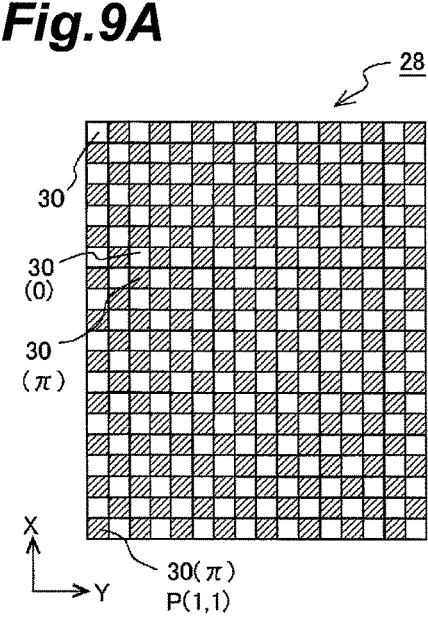
FIG. 9A is a partial view showing a first phase distribution set by the spatial light modulator 28 in the third embodiment, FIG. 9B a partially enlarged view showing a second phase distribution set by the spatial light modulator 28, FIG. 9C a drawing showing an intensity distribution of a spatial image corresponding to the phase distribution of FIG. 9A, and FIG. 9D a drawing showing an intensity distribution of a spatial image corresponding to the phase distribution of FIG. 9B.
Figure 9B:
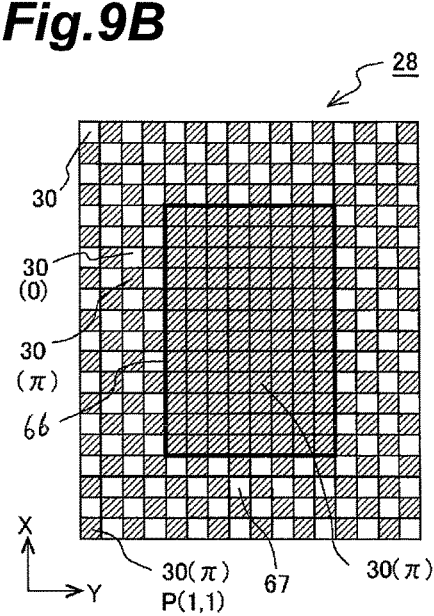
Figure 9C:
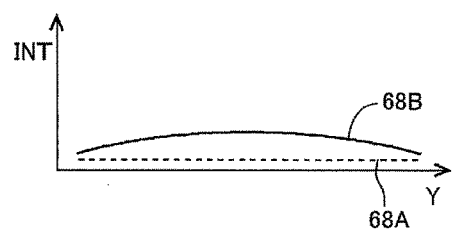
Figure 9D:
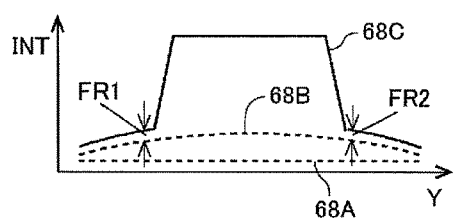

An intensity profile 68B indicated by a solid line in FIG. 9C is an intensity profile INT of a portion along a straight line (axis of measurement) parallel to the Y-axis in the X-directional center part of the spatial image measured by the spatial image measuring apparatus 54. In practice, intensity profiles may be measured along a plurality of straight lines parallel to the Y-axis, which are arranged at predetermined intervals in the X-direction on the entire surface of the spatial image. The measurement result is supplied to the arithmetic apparatus 55. In the present embodiment, an intensity profile 68A of a spatial image corresponding to the phase distribution in FIG. 9A is also preliminarily measured without illumination with the illumination light IL and the measurement result is preliminarily stored in the arithmetic apparatus 55. The arithmetic apparatus 55 calculates a difference between the intensity profile 68B and the intensity profile 68A at each position Y, stores the calculation result as stray light of the spatial light modulator 28, and supplies the result to the main control system 40.

Next, the phase distribution of the array in the illumination region 26A of the mirror elements 30 is set, as shown in FIG. 9B, so that all the mirror elements 30 in a rectangular first region 66 in the center have the phase $\pi$ and so that the mirror elements 30 of phase 0 and the mirror elements 30 of phase $\pi$ are arrayed in a checkered pattern in a second region 67 of a frame shape surrounding the first region 66. Then the spatial image measuring apparatus 54 measures an intensity distribution of an inspection spatial image corresponding to the phase distribution in FIG. 9B. An intensity profile along the aforementioned axis of measurement at this time is at a high level in a portion corresponding to the first region 66, as indicated by a trapezoidal intensity profile 68C in FIG. 9D. The measurement result is supplied to the arithmetic apparatus 55.

Then the arithmetic apparatus 55 calculates differences FR1, FR2 between the intensity profile 68C and the intensity profile 68B of the spatial image corresponding to the phase distribution in FIG. 9A, in level-decreased portions of the intensity profile 68C. The differences FR1, FR2 represent flare of the projection optical system PL. The arithmetic apparatus 55 supplies the differences FR1, FR2 as flare information of the projection optical system PL to the main control system 40. In this manner, the present embodiment allows the inspection apparatus to efficiently inspect the stray light of the spatial light modulator 28 and the flare of the projection optical system PL.

The exposure apparatus may also be configured herein so that if an amount or profile of stray light of the spatial light modulator 28 or an amount or profile of flare of the projection optical system PL exceeds a tolerance, the main control system 40 of the exposure apparatus EX makes information indicative of the fact of exceeding the tolerance, displayed on the display part (monitor) provided on the console of the exposure apparatus EX, or sends the information to the master computer system.

Here, the foregoing tolerance of stray light or flare can be determined by a linewidth error (including OPC error) permitted in the process. Since this linewidth error (OPC error) can be corrected to a certain extent, for example, by change of exposure amount, change of the illumination condition such as pupil luminance distribution, or the like, the main control system 40 of the exposure apparatus EX may be configured to perform the change of exposure amount, or the change of the illumination condition such as the pupil luminance distribution, based on the information about stray light•flare measured. In this case as well, the main control system 40 of the exposure apparatus EX may make the information of these measurements displayed on the display part (monitor) provided on the console of the exposure apparatus EX or may send the information to the master computer system.

It the amount or profile of stray light of the spatial light modulator 28 or the amount or profile of flare of the projection optical system PL still exceeds the tolerance even after the change of exposure amount or the change of the illumination condition such as the pupil luminance distribution, the main control system may make information indicative of the fact of incapability of correction (information to urge replacement of the spatial light modulator 28 or the like) displayed or may send the information to the master computer system.

The above embodiments can be modified as described below.

Since in the above embodiments the spatial image measuring apparatus 54 measures the spatial image of the projection optical system PL, the inspection of the spatial light modulator 28 can be efficiently performed. For measuring a state of the spatial image of the projection optical system PL, a shape of a resist pattern or the like formed after exposure of the photoresist of the wafer W and development of the photoresist may be actually measured, for example, with a scanning electron microscope (SEM) or the like.

Figure 3A:
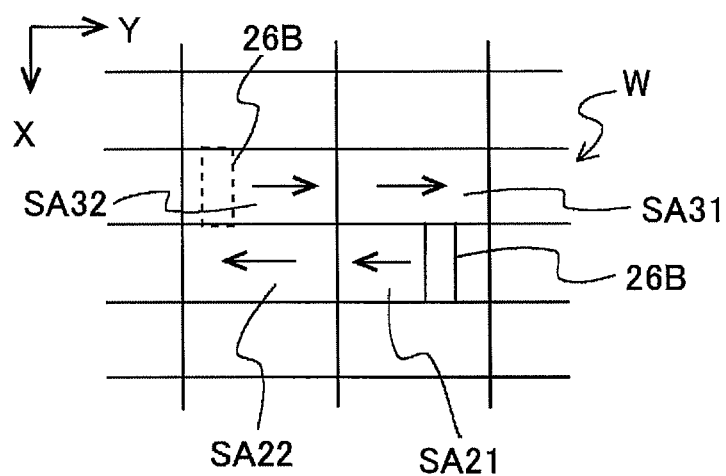
FIG. 3A is a drawing showing shot areas on a wafer in scanning exposure.
Figure 3B:
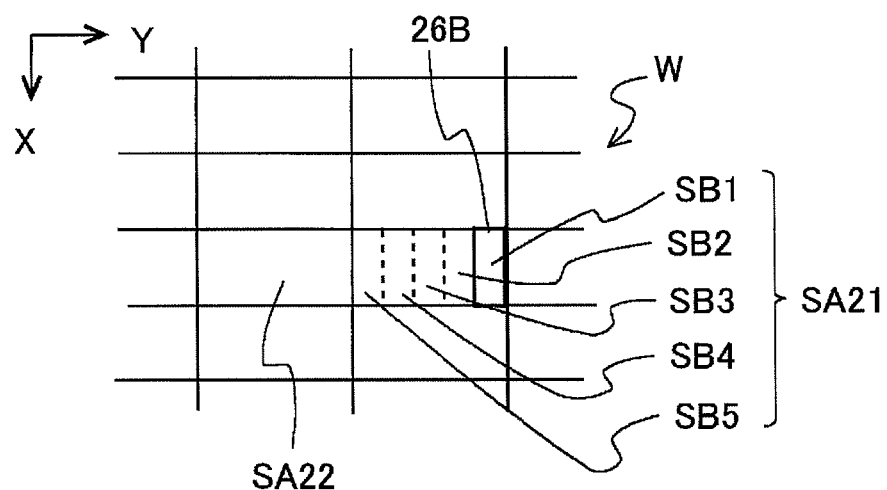
FIG. 3B is a drawing showing shot areas on a wafer in exposure by the step-and-repeat method.

In the above embodiments, the wafer W is continuously moved to implement scanning exposure of the wafer W. In another applicable method, as shown in FIG. 3B, each shot area (e.g., SA21) on the wafer W is divided into a plurality of sub-areas SB1-SB5 or the like in the Y-direction and when the sub-area SB1 or the like reaches the exposure region 26B of the projection optical system PL, a predetermined number of pulses of the illumination light IL are emitted to expose the sub-area SB1 or the like with reflected light from the array of mirror elements 30 of the spatial light modulator 28. After this, the wafer W is stepwise moved in the Y-direction and when the next sub-area SB2 or the like reaches the exposure region 26B, the exposure is carried out in the same manner in the sub-area SB2 or the like. This method is substantially the step-and-repeat method, but the sub-areas SB1-SB5 or the like are exposed with patterns different from each other.

Figure 10:
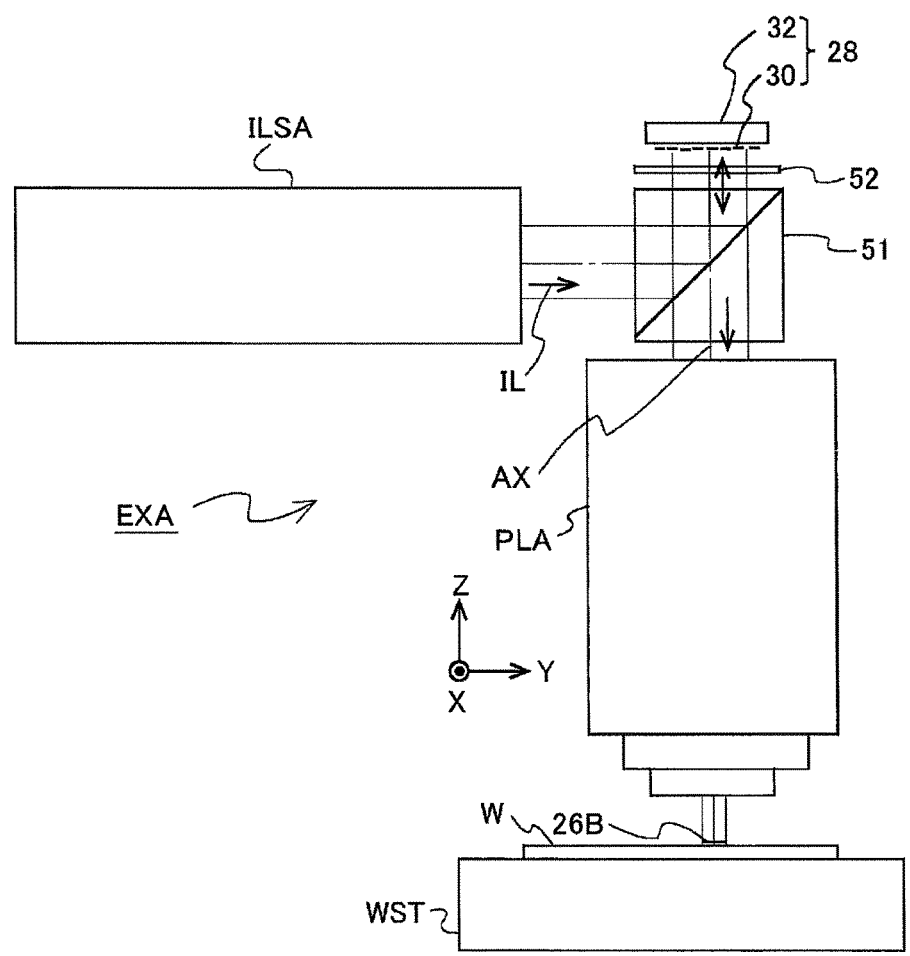
FIG. 10 is a drawing showing a schematic configuration of an exposure apparatus in a modification example.

Next, the above embodiments use the projection optical system PL non-telecentric on the object side. Besides it, it is also possible to use a projection optical system PLA bitelecentric on the object side and on the image side, as shown by an exposure apparatus EXA of a modification example in FIG. 10. In FIG. 10, the exposure apparatus EXA has an illumination optical system ILSA which generates S-polarized illumination light IL approximately in the +Y-direction, a polarization beam splitter 51 which reflects the illumination light IL into the +Z-direction, a quarter wave plate 52 which converts the illumination light IL from the polarization beam splitter 51 into circularly polarized light, the spatial light modulator 28 with the two-dimensional array of the large number of mirror elements 30 which reflects the circularly polarized illumination light IL into the −Z-direction, and the projection optical system PLA which receives the illumination light IL having traveled through the quarter wave plate 52 and the polarization beam splitter 51 after having been reflected by the mirror elements 30 and which projects a spatial image (pattern) onto the exposure region 26B on the surface of the wafer W. The illumination optical system ILSA is an optical system obtained by excluding the mirrors 8B, 8C from the illumination optical system ILS in FIG. 1. The configuration and action of the spatial light modulator 28 are the same as those in the embodiment shown in FIG. 1.

In this modification example, however, the illumination light IL is incident at the incidence angle of approximately 0 to the mirror elements 30 of the spatial light modulator 28. For this reason, in the case of small σ illumination, the reflected light from the mirror elements 30 is incident into the projection optical system PL approximately in parallel with the optical axis AX of the projection optical system PL. Since the exposure apparatus EXA of this modification example allows the use of the bitelecentric projection optical system PLA, the configuration of the exposure apparatus can be simplified.

When the utilization efficiency of illumination light IL is allowed to reduce to half, an ordinary beam splitter may be used instead of the polarization beam splitter 51, without use of the quarter wave plate 52. In this case, polarized illumination is available.

A rod type integrator can also be used as an internal reflection type optical integrator, instead of the microlens array 16 being the wavefront division type integrator in FIG. 1.

Fourth Embodiment

Next, the fourth embodiment will be described with reference to FIGS. 11, 12, and 13A to 14D. In the present embodiment, an independent inspection apparatus is used to measure an average setting error ΔZ of heights of the respective mirror elements (phases of reflected light) in the spatial light modulator (a variation of actual set values from a target value).

Figure 11:
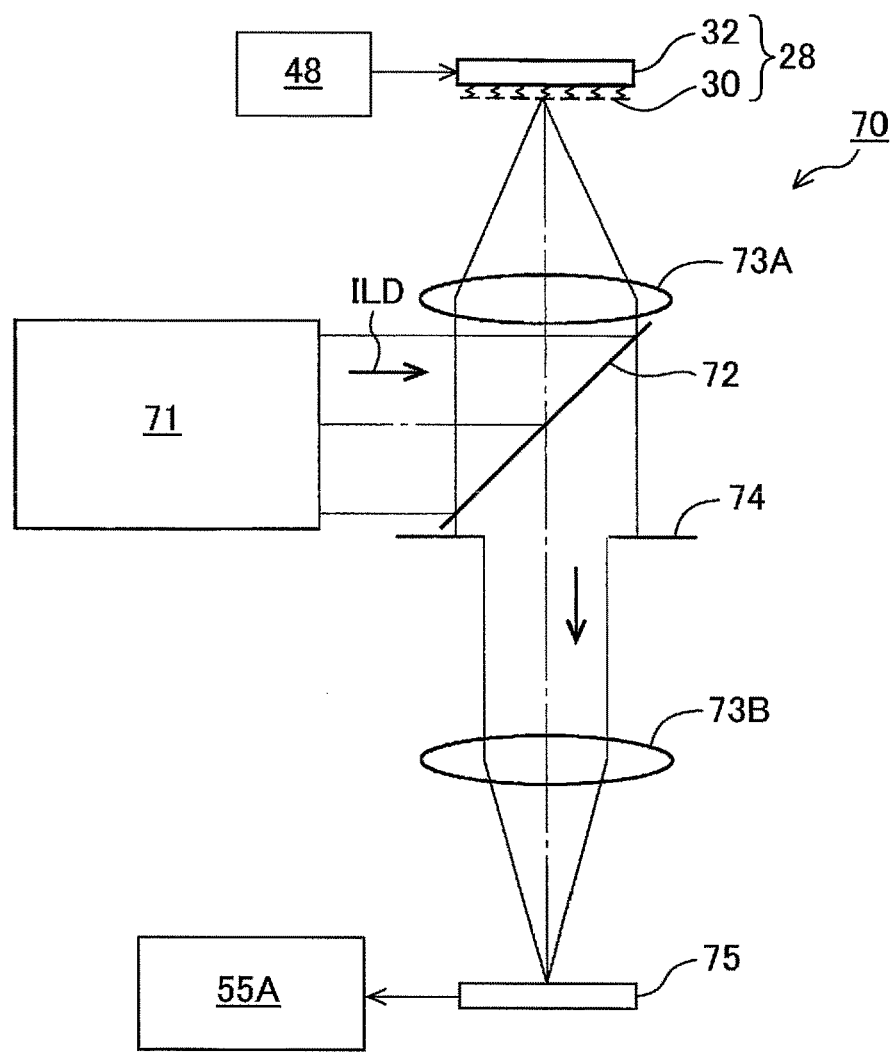
FIG. 11 is a drawing showing an inspection apparatus in the fourth embodiment.

FIG. 11 shows the inspection apparatus 70 of the present embodiment. The inspection apparatus 70 has an illumination system 71 which generates illumination light ILD for inspection, a half mirror 72 which bends the illumination light ILD, and a first objective lens 73A which guides the bent illumination light ILD onto the array of mirror elements 30 of the spatial light modulator 28 as an inspection target. Furthermore, the inspection apparatus 70 has a second objective lens 73B which forms a spatial image of the array of mirror elements 30 from the illumination light having traveled through the first objective lens 73A and the half mirror 72 after having been reflected by the array of mirror elements 30, a variable aperture stop 74 which is arranged on a pupil plane (a plane conjugate with an exit plane) of an inspection optical system (imaging optical system) consisting of the objective lenses 73A, 73B or on a plane near the pupil plane, a two-dimensional image pickup device 75, for example, of a CCD type which takes the spatial image, and an arithmetic apparatus 55A which processes a taken-image signal of the image pickup device 75 to obtain the average setting error ΔZ of heights of the respective mirror elements 30. The main control system 48 is connected to the spatial light modulator 28. The magnification of the inspection optical system is low, e.g., one-fold. The numerical aperture NA of the inspection optical system is variable.

Figure 12:
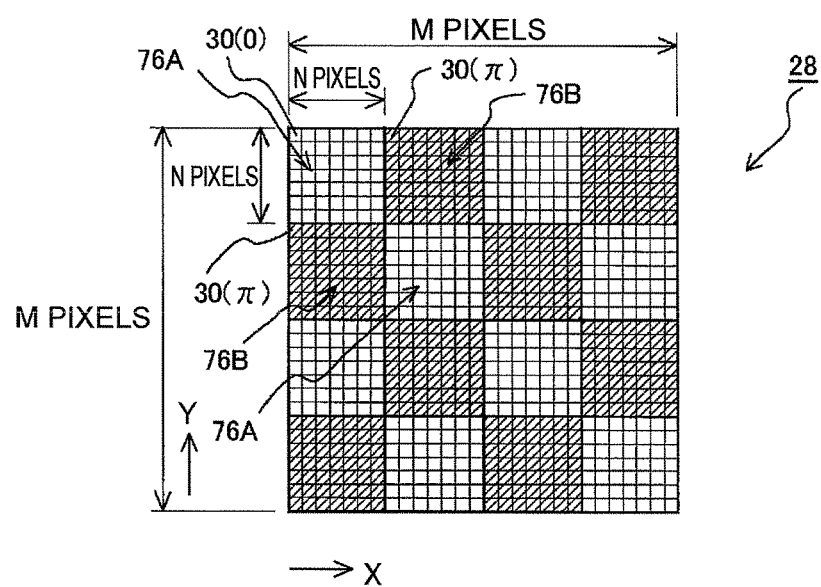
FIG. 12 is a drawing showing an example of a phase distribution set by the spatial light modulator in the fourth embodiment.

In the present embodiment, the distribution of heights of the array of mirror elements 30 of the spatial light modulator 28 (the phase distribution of reflected light) is set, as shown in FIG. 12, in a checkered pattern in units of mirror elements 30 of N×N pixels in N columns in the X-direction and N rows in the Y-direction (N is an integer of not less than 1) as an example. In FIG. 12, when the array of inspection-target mirror elements 30 of M×M pixels in total (M is an integral multiple of N) is divided into pixel groups 76A, 76B arrayed in a checkered pattern so that each pixel group includes N×N mirror elements 30, all the mirror elements 30 in the pixel groups 76A are set in the first state in which the phase of reflected light is changed by the first phase (0° herein). Furthermore, all the mirror elements 30 in the pixel groups 76B alternated with the pixel groups 76A in the X-direction and in the Y-direction are set in the second state in which the phase of reflected light is changed by the second phase (180°=π herein) 180° different from the first phase.

In this case, the numerical aperture NA of the inspection optical system in FIG. 11 is set so as not to resolve images of the respective pixel groups 76A, 76B. Specifically, where the wavelength of the illumination light ILD is denoted by λ, and the pitch of the array of mirror elements 30 by px, the numerical aperture NA can be set in the following range.

$$NA < \lambda(2^{1/2} \cdot N \cdot px) \quad (4)$$

The spatial image of the array of mirror elements 30 was evaluated by simulation on the assumption that the illumination condition of the illumination system 71 in FIG. 11 was one with the coherence factor (a value) being extremely small (approximately 0) and randomly polarized light as an example and that the integer N and the integer M in FIG. 12 were 10 and 100, respectively. On this occasion, the setting error (variation) ΔZ of actual set values from the target value of the heights of the respective mirror elements 30 was assumed to follow a Gaussian distribution and the spatial image detected by the image pickup device 75 in FIG. 11 was obtained by simulation for each of cases where three times the standard deviation of setting error ΔZ (which will be represented by ΔZ3σ hereinafter) was the values shown in FIGS. 13A, 13B, and 13C. FIGS. 13A, 13B, and 13C show an example of distributions of setting errors Δ of the array of mirror elements 30 in FIG. 12 in the cases of ΔZ3σ being 1 nm, 2 nm, and 4 nm, respectively. The distributions of setting errors ΔZ are identical in form with each other but absolute values of setting errors ΔZ are set to increase in proportion to ΔZ3σ. The numerical aperture NA of the inspection optical system in FIG. 11 was set to 0.6 which was almost the largest value in the range satisfying Expression (4).

Figure 14A:
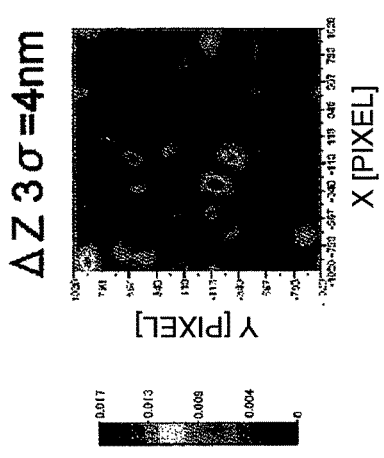
FIG. 14A, FIG. 14B, and FIG. 14C are drawings showing an example of spatial images in the cases where the mirror elements of the spatial light modulator have the height variations of 1 nm, 2 nm, and 4 nm, respectively.
Figure 14B:
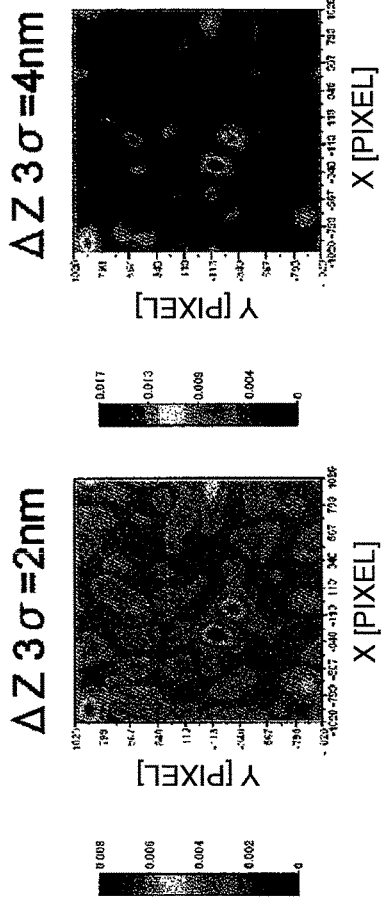
Figure 14C:
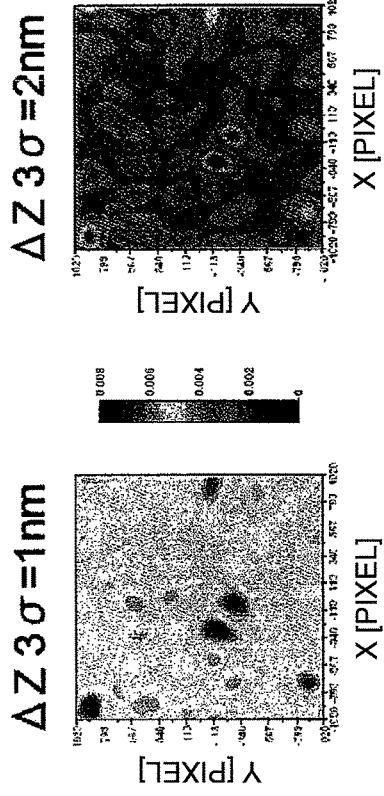

FIGS. 14A, 14B, and 14C show the results obtained by simulation of spatial images (light intensity distributions) acquired by the inspection apparatus 70 in FIG. 11, in the cases where three times the standard deviation of setting errors of heights of the mirror elements 30 in the spatial light modulator 28 (ΔZ3σ) was 1 nm, 2 nm, and 4 nm, respectively. It is seen from FIGS. 14A to 14C that a contrast obtained by dividing a maximum value of the spatial image by an average becomes greater with increase of ΔZ3σ.

Figure 14D:
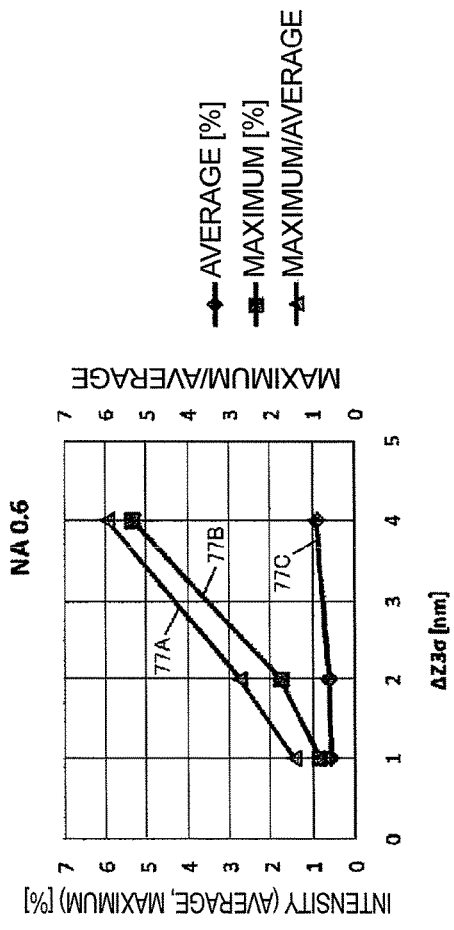
FIG. 14D is a drawing showing an example of relationship between height variations of mirror elements and contrasts of spatial images.

FIG. 14D shows the averages (%) of light intensity of the spatial images in FIGS. 14A to 14C (polygonal line 77C), the maxima (%) of light intensity of those spatial images (polygonal line 77B), and the contrasts (%) obtained by dividing the maxima by the averages of light intensity (polygonal line 77A). It is understood that the contrasts indicated by the polygonal line 77A in FIG. 14D vary approximately in proportion to ΔZ3σ. Then, the information of the polygonal line 77A in FIG. 14D is stored in a memory of the arithmetic apparatus 55A in FIG. 11.

When actually evaluating the setting errors of heights of the mirror elements 30 of the spatial light modulator 28, the arithmetic apparatus 55A obtains the contrast of the image of the array of mirror elements 30 in FIG. 12 from the taken-image signal of the image pickup device 75 in FIG. 11. Furthermore, the arithmetic apparatus applies the contrast to the polygonal line 77A to readily obtain three times the standard deviation of setting errors of heights of the array of mirror elements 30 (ΔZ3σ).

The operation of the inspection apparatus 70 in FIG. 11 can also be performed by the inspection apparatus 54 in the embodiment of FIG. 1. When the inspection apparatus 54 in the embodiment of FIG. 1 is used, the information about the setting errors of heights of the array of mirror elements 30 may be displayed on the display part of the exposure apparatus EX or may be sent to the master computer system.

Figure 15:
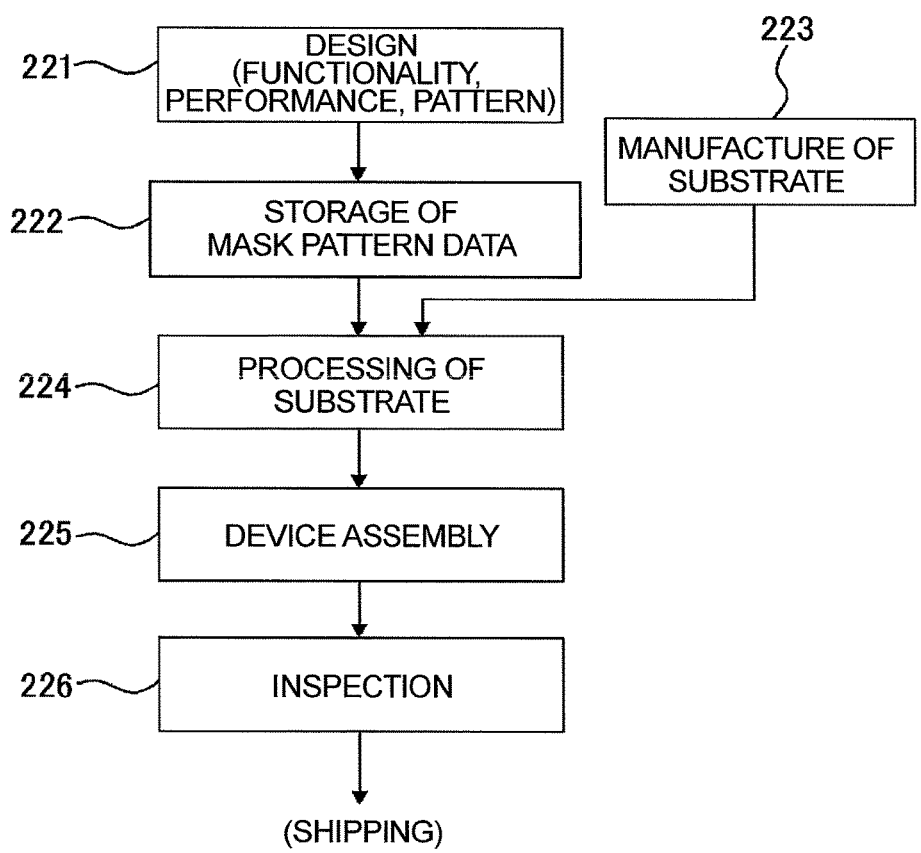
FIG. 15 is a flowchart showing an example of steps for manufacturing electronic devices.

In manufacture of electronic devices (or microdevices), the electronic devices are manufactured, as shown in FIG. 15, through a step 221 to perform design of functionality and performance of the electronic devices, a step 222 to store pattern data of a mask based on this design step, into the main control system of the exposure apparatus EX, EXA in the embodiment, a step 223 to produce a substrate (wafer) as a base material of the devices and coat the substrate with a resist, a substrate processing step 224 including a step of exposing the substrate (photosensitive substrate) with the spatial image of the phase distribution generated in the spatial light modulator 28 by the aforementioned exposure apparatus EX, EXA (or the exposure method), a step of developing the exposed substrate, and heating (curing) and etching steps of the developed substrate, a device assembly step (including processing steps such as a dicing step, a bonding step, a packaging step, and so on) 225, an inspection step 226, and so on.

This device manufacturing method includes the step of exposing the wafer W with the use of the maskless exposure apparatus (or exposure method) of the above embodiment, and the step of processing the exposed wafer W (step 224). Therefore, the electronic devices with fine circuit patterns can be inexpensively manufactured with high accuracy.

The present invention is not limited to the application to semiconductor device manufacturing processes, but the present invention is also widely applicable, for example, to manufacturing processes of liquid crystal display devices, plasma displays, and so on and to manufacturing processes of various devices (electronic devices) such as imaging devices (CMOS type, CCD, etc.), micromachines, MEMS (Microelectromechanical Systems), thin film magnetic heads, and DNA chips.

The present invention is not limited to the above embodiments, but can be realized in various configurations within the scope not departing from the spirit and scope of the present invention.

The present invention can also be described according to the articles below.

1. A method for inspecting a spatial light modulator having an array of optical elements to be illuminated with light, the inspection method for the spatial light modulator comprising:
    performing such control that in at least a partial inspection target area in the array of optical elements, the optical elements in a first state and the optical elements in a second state which allow incident light to pass with a phase change of a second phase 180° different from a first phase which is a phase of light having passed the optical elements in the first state, become arrayed in a checkered pattern;
    guiding light having passed the inspection target area, to an image plane of a projection optical system;
    guiding the light to the projection optical system with a resolution limit coarser than a width of an image of one mentioned optical element to form a spatial image; and
    inspecting a characteristic of the spatial light modulator from light having passed the projection optical system, wherein the following relation is satisfied:

$$\lambda/(2 \cdot NA) > \beta \cdot py,$$

where
$\lambda$: a wavelength of the light,
NA: a numerical aperture on the image plane side of the projection optical system in guiding the light to the image plane of the projection optical system, $\beta$: a magnification of the projection optical system, and
py: a width of the array of optical elements.

2. The method for inspecting the spatial light modulator according to Article 1, wherein for inspecting the characteristic of the spatial light modulator, an optical element with a defect in the inspection target area is specified from the spatial image formed by the projection optical system.

3. The method for inspecting the spatial light modulator according to Article 2, wherein for specifying the optical element with the defect, a position of an optical element corresponding to a portion where a light intensity is stronger than a predetermined threshold in the spatial image is obtained in the inspection target area.

4. The method for inspecting the spatial light modulator according to Article 2 or 3, comprising:
    dividing the inspection target area into a first region and a second region each of which includes a plurality of mentioned optical elements and which are adjacent in a first direction being an array direction of the optical elements; and
    when the optical element with the defect is located in the first region, defining an optical element located away in the first direction from the optical element with the defect in the second region, as a substitute optical element for the optical element with the defect.

5. The method for inspecting the spatial light modulator according to Article 1, wherein for inspecting the characteristic of the spatial light modulator, distortion information of a reflective surface of the optical elements in the inspection target area is obtained from the spatial image formed by the projection optical system.

6. The method for inspecting the spatial light modulator according to Article 5, wherein a stress is applied to the inspection target area of the spatial light modulator, based on the distortion information of the reflective surface.

7. The method for inspecting the spatial light modulator according to Article 1, wherein for inspecting the characteristic of the spatial light modulator, an amount of stray light caused by the spatial light modulator is obtained from the spatial image formed by the projection optical system.

8. The method for inspecting the spatial light modulator according to Article 7, comprising:
dividing the inspection target area into a first illumination region and a second illumination region surrounding the first illumination region;
setting the optical elements in the first illumination region into the first state, and setting the second illumination region into a state in which the optical elements in the first state and the optical elements in the second state are arrayed in the checkered pattern;
forming an inspection spatial image via the projection optical system from the light having passed the inspection target area; and obtaining flare information of the projection optical system from the spatial image and the inspection spatial image formed by the projection optical system.

9. The method for inspecting the spatial light modulator according to Article 1, wherein for inspecting the characteristic of the spatial light modulator, a variation in phase of light passing the optical elements of the spatial light modulator is obtained from a contrast of light intensity of the spatial image formed by the projection optical system.

10. The method for inspecting the spatial light modulator according to any one of Articles 1 to 9, wherein inspecting the characteristic of the spatial light modulator from the spatial image includes optically detecting the spatial image.

11. An exposure method for exposing a substrate with exposure light via a spatial light modulator having an array of optical elements and via a projection optical system, the exposure method comprising:
a step of performing an inspection of the spatial light modulator by the method for inspecting the spatial light modulator according to any one of Articles 1 to 10.

12. The exposure method according to Article 11, wherein a numerical aperture on the image plane side of the projection optical system in guiding the light to the image plane of the projection optical system is set lower than a numerical aperture on the image plane side of the projection optical system in exposing the substrate.

13. An apparatus for inspecting a spatial light modulator having an array of optical elements to be illuminated with light, the inspection apparatus for the spatial light modulator comprising:
an illumination apparatus which illuminates at least a partial inspection target area in the array of optical elements;
a control apparatus which performs such control that in the inspection target area, the optical elements in a first state and the optical elements in a second state which allow incident light to pass with a phase change of a second phase 180° different from a first phase being a phase of light having passed the optical elements in the first state become arrayed in a checkered pattern;
a projection optical system which guides light having passed the inspection target area, to an image plane; and
an arithmetic apparatus which performs an inspection of the spatial light modulator, using light having passed the projection optical system, wherein the following relation is satisfied:

$$\lambda/(2 \cdot NA) > \beta \cdot py,$$

where
$\lambda$: a wavelength of the light,
NA: a numerical aperture on the image plane side of the projection optical system in guiding the light to the image plane of the projection optical system,
$\beta$: a magnification of the projection optical system, and
py: a width of the array of optical elements.

14. The apparatus for inspecting the spatial light modulator according to Article 13, wherein the arithmetic apparatus specifies an optical element with a defect in the inspection target area.

15. The apparatus for inspecting the spatial light modulator according to Article 14, wherein the control apparatus operates as follows:
the control apparatus divides the inspection target area into a first region and a second region each of which includes a plurality of mentioned optical elements and which are adjacent in a first direction being an array direction of the optical elements; and
when the optical element with the defect is located in the first region, the control apparatus defines an optical element located away in the first direction from the optical element with the defect in the second region, as a substitute optical element for the optical element with the defect.

16. The apparatus for inspecting the spatial light modulator according to Article 13, wherein the arithmetic apparatus obtains distortion information of a reflective surface of the optical elements in the inspection target area.

17. The apparatus for inspecting the spatial light modulator according to Article 13, wherein the arithmetic apparatus obtains an amount of stray light caused by the spatial light modulator.

18. The apparatus for inspecting the spatial light modulator according to Article 17,
wherein the control apparatus operates as follows:
the control apparatus divides the inspection target area into a first region and a second region surrounding the first region;
the control apparatus sets the optical elements in the first region into the first state, and sets the second region into a state in which the optical elements in the first state and the optical elements in the second state are arrayed in the checkered pattern; and
wherein the arithmetic apparatus obtains flare information of the projection optical system, based on an inspection spatial image formed via the projection optical system from light having passed the first region and the second region and based on the spatial image.

19. The apparatus for inspecting the spatial light modulator according to Article 13, wherein the arithmetic apparatus obtains a variation of phase of light passing the optical elements of the spatial light modulator from a contrast of light intensity of the spatial image formed by the projection optical system.

20. An exposure apparatus for exposing a substrate with exposure light from an illumination system via a projection system, the exposure apparatus comprising:
a spatial light modulator which is arranged on the object plane side of the projection system and which has an array of optical elements each of which can be controlled so as to guide the exposure light to the projection system; and the apparatus for inspecting the spatial light modulator according to any one of Articles 13 to 19.

21. The exposure apparatus according to Article 20, wherein the illumination system also serves as at least a part of the illumination apparatus of the inspection apparatus, and wherein the projection system also serves as the projection optical system of the inspection apparatus.

22. The exposure apparatus according to Article 20 or 21, wherein a numerical aperture on the image plane side of the projection optical system in performing the inspection of the spatial light modulator with use of the light guided to the image plane of the projection optical system is set lower than a numerical aperture on the image plane side of the projection optical system in exposing the substrate.

23. A device manufacturing method comprising:
forming a pattern of a photosensitive layer on a substrate, using the exposure method according to Article 11 or 12; and
processing the substrate with the pattern formed thereon.

24. A device manufacturing method comprising:
forming a pattern of a photosensitive layer on a substrate, using the exposure apparatus according to any one of Articles 20 to 22; and
processing the substrate with the pattern formed thereon.

The disclosures in the foregoing Publications, International Publications, U.S. Patents, or U.S. Pat. Published Applications cited in the present specification are incorporated as part of the description of the present specification. The entire disclosure contents in Japanese Patent Application No. 2011-191319 filed on Sep. 2, 2011 including the specification, the scope of claims, the drawings, and the abstract are incorporated herein by reference in their entirety.

REFERENCE SIGNS LIST

EX, EXA exposure apparatus; ILS, ILSA illumination optical system; PL, PLA projection optical system; W wafer; 28 spatial light modulator; 30 mirror element; 37A regular region; 37B preparatory region; 38 defective element; 39 substitute element; 48 modulation control unit; 53 inspection apparatus; 54 spatial image measuring apparatus.

The invention claimed is:

1. An exposure apparatus for exposing an object, comprising:
an illumination system which supplies exposure light;
a spatial light modulator having a base and a plurality of mirrors, each reflecting the exposure light, each of the plurality of mirrors being arranged on the base in parallel with the base;
a projection optical system which projects a pattern onto the object with the exposure light by way of the spatial light modulator;
a base-adjustment system adapted to deform the base, at different positions on the base, in a direction along an optical axis of the projection optical system; and
an inspecting system which inspects information regarding the flatness of the base to be used for the base-adjustment system deforming the base, the inspecting system including a light receiver which receives light from the plurality of mirrors of the spatial light modulator by way of the projection optical system and provides an output regarding the flatness state of the base.

2. The exposure apparatus according to claim 1, wherein the base-adjustment system deforms the base so as to flatten the base.

3. The exposure apparatus according to claim 2, wherein each of the plurality of mirrors of the spatial light modulator is selectively set in one of a first state and a second state, the first state defined as a state in which light from the illumination system is reflected, the second state defined as a state in which the light from the illumination system is reflected so that the light from the illumination system has a phase difference with respect to the light reflected by the first state mirrors, and the light receiver receives light from the spatial light modulator, the spatial light modulator being set so that the first state mirrors and the second state mirrors are alternately located.

4. The exposure apparatus according to claim 1, wherein the base-adjustment system has a stress applying system which applies a stress to the base.

5. A device manufacturing method comprising:
forming a pattern of a photosensitive layer on a substrate, using the exposure apparatus as set forth in claim 1; and
processing the substrate on which the pattern is formed.

6. An exposure method for exposing an object, comprising:
supplying exposure light;
providing a spatial light modulator having a base and a plurality of mirrors, each reflecting the exposure light, each of the plurality of mirrors being arranged on the base in parallel with the base;
projecting a pattern onto the object with the exposure light, using a projection optical system;
deforming the base, at different positions on the base, in a direction along an optical axis of the projection optical system; and
inspecting information regarding the flatness of the base to be used for the deforming, the inspecting comprising receiving light from the plurality of mirrors of the spatial light modulator by way of the projection optical system and providing an output regarding the flatness state of the base.

7. The exposure method according to claim 6, wherein the deforming flattens the base.

8. The exposure method according to claim 7, wherein each of the plurality of mirrors of the spatial light modulator is selectively set in one of a first state and a second state, the first state defined as a state in which light from an illumination system supplying the exposure light is reflected, the second state defined as a state in which the light from the illumination system is reflected so that the light from the illumination system has a phase difference with respect to the light reflected by the first state mirrors, and wherein
the spatial light modulator is set so that the first state mirrors and the second state mirrors are alternately located.

9. The exposure method according to claim 6, wherein the deforming includes applying a stress to the base.

10. A device manufacturing method comprising:
forming a pattern of a photosensitive layer on a substrate, using the exposure method as set forth in claim 6; and
processing the substrate on which the pattern is formed.

* * * * *